US008153400B1

(12) United States Patent
Scharenberg

(10) Patent No.: US 8,153,400 B1
(45) Date of Patent: Apr. 10, 2012

(54) **NUCLEIC ACIDS ENCODING A *MUTT* DOMAIN-CONTAINING POLYPEPTIDE**

(75) Inventor: Andrew M. Scharenberg, Seattle, WA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 09/958,184

(22) PCT Filed: Apr. 26, 2000

(86) PCT No.: PCT/US00/11319
§ 371 (c)(1),
(2), (4) Date: Aug. 12, 2002

(87) PCT Pub. No.: WO00/65056
PCT Pub. Date: Nov. 2, 2000

Related U.S. Application Data

(60) Provisional application No. 60/131,051, filed on Apr. 26, 1999.

(51) Int. Cl.
*C12N 15/09* (2006.01)
(52) U.S. Cl. ............ 435/69.2; 435/6; 435/18; 435/69.1; 530/350
(58) Field of Classification Search ................. 429/94.5, 429/94.6; 435/6, 183, 193, 195; 530/350
See application file for complete search history.

(56) References Cited

U.S. PATENT DOCUMENTS 5,580,723 A    12/1996  Wells et al. ........................ 435/6

FOREIGN PATENT DOCUMENTS

| EP | 1171601 B1 | 10/2006 |
| WO | WO 96/15222 | 5/1996 |
| WO | WO 00/29571 | 5/2000 |
| WO | WO 00/40614 | 7/2000 |
| WO | WO 00/65056 A2 | 11/2000 |

OTHER PUBLICATIONS

Zhu et al., Cell, vol. 85, pp. 661-671, 1996.*
Santella et al., FASEB J. vol. 11, pp. 1091-1109, 1997.*
Ames et al., The role of polyamines in the neutralization of bacteriophage deoxyribonucleic acid, *Journal of Biological Chemistry*, 235: 769-775, 1960.
Bessman et al., The MutT proteins or "Nudix" hydrolases, a family of versatile, widely distributed, "housecleaning" enzymes, *Journal of Biological Chemistry*, 271: 25059-25062, 1996.
Bhatnagar et al., Characterization of the mutT nucleoside triphosphatase of *Escherichia coli*, *Journal of Biological Chemistry*, 266: 9050-9054, 1991.
Chakraborti et al., Oxidant, mitochondria and calcium: an overview, *Cell Signal*, 11: 77-85, 1999.
Dousa et al., Adenine nucleotide diphosphates: emerging second messengers acting via intracellular Ca2+ release, *American Journal of Physiology*, 271: C1007-C1024, 1996.

GenBank Submission; NIH/NCBI; Accession No. AI565810; Strausburg; 1998 (last submission).
GenBank Submission; NIH/NCBI; Accession No. W05526; Wilson; 1995 (last submission).
Kisselev et al., Diadenosine oligophosphates ($Ap_nA$), a novel class of signalling molecules?, *FEBS Letters*, 427: 157-163, 1998.
Koch-Nolte et al., Mono(ADP-ribosyl)transferases and related enzymes in animal tissues. Emerging gene families, *Advances in Experimental Medicine and Biology*, 419: 1-13, 1997.
Liang et al., Synthesis of NAADP and cADPR in mitochondria, *Archives of Biochemistry and Biophysics*, 371: 317-325, 1999.
Lin, J. et al., The role of Glu 57 in the mechanism of the *Escheria coli* MutT enzyme by mutagenesis and heteronuclear NMR. *Biochemistry* 35: 6715-6726, 1996.
Liu et al., Induction of apoptotic program in cell-free extracts: requirement for dATP and cytochrome c, *Cell*, 86: 147-157, 1996.
McConkey et al., Signal transduction pathways in apoptosis, *Stem Cells*, 14: 619-631, 1996.
McLennan et al., The MutT Motif Family of Nucleotide Phosphohydrolases in Man and Human Pathogens (Review), *International Journal of Molecular Medicine*, 4(1): 79-89, 1999.
Mo et al., Hydrolytic elimination of a mutagenic nucleotide, 8-oxodGTP, by human 18-kilodalton protein: sanitization of nucleotide pool, *Proceedings of the National Academy of Science USA*, 89: 11021-11025, 1992.
Nagamine et al., Molecular cloning of a novel putative $Ca^{2+}$ channel protein (TRPC7) highly expressed in brain, *Genomics*, 54: 124-131, 1998.
O'Handley et al., *Escherichia coli* orf17 codes for a nucleoside triphosphate pyrophosphohydrolase member of the MutT family of proteins. Cloning, purification, and characterization of the enzyme, *Journal of Biological Chemistry*, 271: 24649-24654, 1996.
O'Handley et al., Orf186 represents a new member of the Nudix hydrolases, active on adenosine(5')triphospho(5')adenosine, ADP-ribose, and NADH, *Journal of Biological Chemistry*, 273: 3192-3197, 1998.
Okazaki et al., Glycosylphosphatidylinositol-anchored and secretory isoforms of mono-ADP-ribosyltransferases, *Journal of Biological Chemistry*, 273: 23617-23620, 1998.
Prosite online: Entry PDOC00695 (Koonin et al.), Nov. 1997.
Sheikh et al., Identification and Characterization of the Nudix Hydrolase from the Archaeon, Methancoccus jannaschii, as a Highly Specific ADP-ribose Pyrophosphatase, *Journal of Biological Chemistry*, 273(33): 20924-20928, 1998.

(Continued)

*Primary Examiner* — Richard Hutson
(74) *Attorney, Agent, or Firm* — Wolf, Greenfield & Sacks, P.C.

(57) ABSTRACT

The invention pertains to nucleic acids encoding a mutT domain-containing polypeptide, including fragments and biologically functional variants thereof. The invention also pertains to therapeutics and diagnostics involving the foregoing polypeptide and nucleic acids and agents that bind the foregoing polypeptide and nucleic acids. The invention also pertains to the identification of a novel mutT domain in human TrpC7, a polypeptide previously described as a putative calcium ion channel. Accordingly, the invention also pertains to methods and compositions for identifying agents useful modulating mutT domain-mediated calcium or other ion transport in cells expressing a polypeptide comprising a mutT domain and a calcium or other ion channel.

7 Claims, 2 Drawing Sheets

OTHER PUBLICATIONS

Swissprot online: AC Q09297 (Chissoe et al.), Jun. 2002.

Thorne et al., Human diadenosine 5',5'-$P^1$,$P^4$-tetraphosphate pyrophosphohydrolase is a member of the MutT family of nucleotide pyrophosphatases, *Biochemistry Journal*, 311: 717-721, 1995.

Wilding et al., ADP-ribose gates the fertilization channel in ascidian oocytes, *American Journal of Physiology*, 275: C1277-C1283, 1998.

WPI Database: Section Ch, Week 200033 (see WO 00/29571), XP 002154041, Nov. 2000.

Zucchi et al., The Sarcoplasmic Reticulum $Ca^{2+}$ Channel/Ryanodine Receptor: Modulation by Endogenous Effectors, Drugs, and Disease States, *Pharmacology Reviews*, 49(1): 1-51, 1997.

Hunter, J.J. et al., Chromosomal localization and genomic characterization of the mouse melastatin gene (Mlsn1). Genomics. Nov. 15, 1998;54(1):116-23.

Safrany, S.T. et al., A novel context for the 'MutT' module, a guardian of cell integrity, in a diphosphoinositol polyphosphate phosphohydrolase. EMBO J. Nov. 16, 1998;17(22):6599-607.

Scharenberg, A.M. et al., Reconstitution of interactions between tyrosine kinases and the high affinity IgE receptor which are controlled by receptor clustering. EMBO J. Jul. 17, 1995;14(14):3385-94.

* cited by examiner

NUCLEIC ACIDS ENCODING A *MUTT* DOMAIN-CONTAINING POLYPEPTIDE

RELATED APPLICATIONS

This application is a national stage filing 35 U.S.C. §120 or 35 U.S.C. §365(c) of PCT International application PCT/US00/11319 designating the United States of America, and filed Apr. 26, 2000, of which this application is a national stage filing under 35 U.S.C. §371, was published under PCT Article 21(2) in English.

This application claims priority benefits under 35 U.S.C. §119(e) to U.S. Provisional Application Ser. No. 60/131,051 filed Apr. 26, 1999, entitled NUCLEIC ACIDS ENCODING A MutT DOMAIN-CONTAINING POLYPEPTIDE, by Andrew M. Scharenberg, and is hereby incorporated by reference.

FIELD OF THE INVENTION

This invention relates to nucleic acids encoding a mutT domain-containing polypeptide, including fragments and biologically functional variants thereof, and nucleic acids and agents that bind the foregoing polypeptide and nucleic acids.

BACKGROUND OF THE INVENTION

MutT is an enzyme first identified in *Escherichia coli* that reportedly dephosphorylates 8-oxo-dGTP, a metabolite known to promote high levels of AT to CG transversion mutations (Bhatnagar et al., *J Biol. Chem.,* 1991, 266:9050-4). A mutT strain of *Escherichia coli* that lacks this catalytic activity has an increased spontaneous mutation rate of up to $10^4$-fold (Bessman et al., *J Biol Chem.,* 1996, 271:25059-62). Mammalian counterparts of this important antimutator dGTPase have been identified (Mo et al., *Proc Natl Acad Sci USA.,* 1992, 89:11021-51992).

More recently, additional polypeptides sharing a small, localized region of homology with MutT have been identified. This region of homology is referred to herein as the MutT domain, with a sequence of GXXXXX-EXXXXXXREXXEEXXX (SEQ ID NO. 4), wherein the X residues in positions 2-6,8-14, 18, and 21-22 represent any amino acid and the X residues in positions 17 and 23 represent amino acids with an aliphatic side chain. Members of this newly identified MutT family of polypeptides are believed to act as homeostatic checkpoints at some important stages in the nucleoside phosphate metabolic pathways, guarding against the potentially dangerous consequences of elevated levels of a small number of these intermediates (Bessman et al., supra; O'Handley et al., *J Biol Chem.,* 1998, 273:3192-7).

Certain other MutT family members have been proposed to protect the cell from the deleterious consequences of inappropriate activation of some signal transduction processes, by catabolizing additional nucleoside phosphates that may have cell signaling roles (Bessman et al., supra). For example, hydrolysis of dATP by the MutT module (O'Handley et al., *J Biol Chem.,* 1996, 271:24649-54) may, in mammals, guard against this molecule providing an untimely initiation of apoptosis (Liu et al., *Cell,* 1996, 86:147-57). Diadenosine polyphosphates, which mediate cellular stress responses (Kisselev et al., *FEBS Lett,* 1998, 427:157-63), are also metabolized by this protein family (Thorne et al., *Biochem J,* 1995, 311 (Pt 3):717-21). To date, ~15 MutT family members have been characterized, all of which appear dedicated to the metabolism of nucleoside phosphates (Bessman et al., supra).

Despite the foregoing similarities, MutT family members appear to vary in their substrate specificity. MutT substrates reportedly include nucleoside triphosphates, coenzymes, nucleotide sugars, and dinucleoside polyphosphates. It has therefore been suggested that these enzymes are involved in diverse metabolic pathways, and function by cleansing the cell of potentially deleterious endogenous metabolites, and/or modulate the accumulation of intermediates in biochemical pathways.

SUMMARY OF THE INVENTION

The molecular cloning and characterization of mutTCCH-1 (alternatively referred to as NUDT9), a novel molecule that contains a variant of a mutT domain, is disclosed herein.

Accordingly, the invention provides an isolated mutTCCH-1 nucleic acid molecule, unique fragments of the foregoing mutTCCH-1 molecule, expression vectors containing the foregoing, and host cells transfected with these molecules. The invention also provides isolated binding polypeptides and binding agents which bind such polypeptides, including antibodies. The foregoing can be used, inter alia, in the diagnosis or treatment of conditions characterized by the aberrant expression levels and/or the presence of mutant forms of a mutTCCH-1 nucleic acid or polypeptide. The invention also provides methods for identifying agents useful in the diagnosis or treatment of such conditions.

The identification, surprisingly, of a novel mutT domain in human TrpC7 (SEQ ID NO:6) a polypeptide previously described as a putative $Ca^{2+}$ channel protein, is also disclosed. It was discovered, unexpectedly, that the mutT domain is a mediator of signals that modulate the transport of calcium ions in and out of a cell expressing such polypeptide. Accordingly, the invention also provides methods and compositions for identifying agents useful in modulating mutT domain-mediated calcium or other ion transport in cells expressing such polypeptide.

Throughout this application, reference is made to measuring/detecting calcium channel activity. It is to be understood that the transport of ions other than calcium, e.g. Mg, Zn, Sr, Mn, can be measured/detected within the meaning and scope of the present invention.

According to one aspect of the invention, isolated nucleic acid molecules that code for a mutTCCH-1 polypeptide are provided and include: (a) nucleic acid molecules which hybridize under stringent conditions to a molecule consisting of a nucleic acid of SEQ ID NO:1 and which code for a mutTCCH-1 polypeptide having pyrophosphohydrolase and/or sugar-phosphate hydrolase activity (collectively referred to as "hydrolase activity"), (b) deletions, additions and substitutions of (a) which code for a respective mutTCCH-1 polypeptide having any of the foregoing hydrolase activity, (c) nucleic acid molecules that differ from the nucleic acid molecules of (a) or (b) in codon sequence due to the degeneracy of the genetic code, and (d) full-length complements of (a), (b) or (c). In certain embodiments, the isolated nucleic acid molecule comprises nucleotides 1-1718 of SEQ ID NO:1. In some embodiments the isolated nucleic acid molecules are those comprising the human cDNA or gene corresponding to SEQ ID NO:3. The isolated nucleic acid molecule also can comprise a molecule which encodes the polypeptide of SEQ ID NO:2 having pyrophosphohydrolase and/or sugar-phosphate hydrolase activity. In preferred embodiments, the isolated nucleic acid molecule encodes a polypeptide having ADP-ribose hydrolase activity.

The invention in another aspect provides an isolated nucleic acid molecule selected from the group consisting of (a) a unique fragment of nucleic acid molecule of SEQ ID NO:1 (of sufficient length to represent a sequence unique within the human genome), (b) full-length complements of (a), provided that the fragment includes a sequence of contiguous nucleotides which is not identical to a sequence selected from the sequence group consisting of (1) sequences having the GenBank and EMBL accession numbers of Table I, (2) full-length complements of (1), and (3) fragments of (1) and (2).

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In another embodiment, the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

According to another aspect, the invention provides expression vectors, and host cells transformed or transfected with such expression vectors, comprising the nucleic acid molecules described above.

According to another aspect of the invention, an isolated polypeptide is provided. The isolated polypeptide is encoded by the foregoing isolated nucleic acid molecules of the invention. In some embodiments, the isolated polypeptide is encoded by the nucleic acid of SEQ ID NO:1, giving rise to a polypeptide having the sequence of SEQ ID NO:2 that has hydrolase activity. In other embodiments, the isolated polypeptide may be a fragment or variant of the foregoing of sufficient length to represent a sequence unique within the human genome, and identifying with a polypeptide that has hydrolase activity, provided that the fragment includes a sequence of contiguous amino acids which is not identical to any sequence encoded for by the nucleic acid sequence identified in Table I. In another embodiment, immunogenic fragments of the polypeptide molecules described above are provided.

According to another aspect of the invention, isolated binding polypeptides are provided which selectively bind a polypeptide encoded by the foregoing isolated nucleic acid molecules of the invention. Preferably the isolated binding polypeptides selectively bind a polypeptide which comprises the sequence of SEQ ID NO:2, or fragments thereof. In preferred embodiments, the isolated binding polypeptides include antibodies and fragments of antibodies (e.g., Fab, $F(ab)_2$, Fd and antibody fragments which include a CDR3 region which binds selectively to the mutTCCH-1 polypeptide). In certain embodiments, the antibodies are human.

Another aspect of the invention is a method for determining the level of mutTCCH-1 expression in a subject. The method involves: (a) measuring expression of mutTCCH-1 in a test sample, and (b) comparing the measured expression of mutTCCH-1 in the test sample to mutTCCH-1 expression in a control containing a known level of mutTCCH-1 expression to determine the level of mutTCCH-1 expression in the subject. Expression is defined as mutTCCH-1 mRNA expression, mutTCCH-1 polypeptide expression, or mutTCCH-1 activity as defined elsewhere herein. Various methods can be used to measure expression. Preferred embodiments of the invention include PCR and Northern blotting for measuring mRNA expression, monoclonal or polyclonal mutTCCH-1 antisera as reagents to measure mutTCCH-1 polypeptide expression, as well as methods for measuring mutTCCH-1 hydrolase activity.

In important embodiments, when mutTCCH-1 hydrolase activity is measured as an indicator of mutTCCH-1 expression, a nucleotide sugar is used as a substrate. In preferred embodiments, the nucleotide sugar is ADP-ribose.

In certain embodiments, test samples such as biopsy samples, and biological fluids such as blood, are used as test samples. MutTCCH-1 expression in a test sample of a subject is compared to mutTCCH-1 expression in control.

The invention in another aspect involves a method for increasing mutTCCH-1 expression in a subject that expresses a mutant mutTCCH-1. An isolated mutTCCH-1 nucleic acid molecule of the invention or an expression product thereof is administered to a subject expressing a mutant mutTCCH-1, in an amount effective to increase wild-type mutTCCH-1 expression in the subject.

Another aspect of the invention provides compositions comprising any of the foregoing isolated nucleic acid molecules of the invention, or expression products thereof, and which increase expression of mutTCCH-1 (wild-type), and a pharmaceutically acceptable carrier.

According to still another aspect of the invention, a method is provided for identifying lead compounds for an agent useful in the diagnosis or treatment of disease associated with pyrophosphohydrolase and/or sugar-phosphate hydrolase activity. The method involves forming a mixture of a mutTCCH-1 polypeptide, a ligand that associates with a mutTCCH-1 polypeptide (such as a nucleoside triphosphate, a mutTCCH-1 coenzyme, a nucleotide sugar, a dinucleoside polyphosphate, etc.), and a candidate agent. The mixture is incubated under conditions which, in the absence of the candidate agent, permit specific binding of the ligand that associates with a mutTCCH-1 polypeptide to the mutTCCH-1 polypeptide. A reference specific association of the ligand that associates with a mutTCCH-1 polypeptide to the mutTCCH-1 polypeptide is then detected. Detection of an increase in the foregoing activity relative to the reference specific association in the presence of the candidate agent indicates that the candidate agent is an agent which increases a mutTCCH-1 activity, such as pyrophosphohydrolase and/or sugar-phosphate hydrolase activity. Detection of a decrease in the foregoing activities relative to the reference specific association in the presence of the candidate agent indicates that the candidate agent is an agent which decreases a mutTCCH-1 activity, such as pyrophosphohydrolase and/or sugar-phosphate hydrolase activity. Preferred mutTCCH-1 polypeptides include the polypeptides encoded by any of the foregoing isolated nucleic acid molecules of the invention (SEQ ID NO:1, SEQ ID NO:3 and/or SEQ ID NO:5), or fragments of the foregoing polypeptides, with pyrophosphohydrolase and/or sugar-phosphate hydrolase activity. In important embodiments, the ligand that associates with a mutTCCH-1 polypeptide is a nucleotide sugar. In preferred embodiments, the ligand that associates with a mutTCCH-1 polypeptide is ADP-ribose.

According to another aspect of the invention, a method for identifying agents useful in the modulation of calcium or other ion channel activity in a polypeptide comprising a calcium channel and a mutT domain, is provided. The method involves forming a mixture of a polypeptide comprising a calcium channel and a mutT domain, a ligand that associates with the mutT domain of said polypeptide (such as a nucleoside triphosphate, a nucleotide sugar, a dinucleoside polyphosphate, etc.), and a candidate agent. The mixture is incubated under conditions which, in the absence of the candidate agent, permit specific binding of the ligand to the mutT domain of said polypeptide. A reference specific $Ca^{2+}$ or other ion concentration associated with calcium channel activity of said polypeptide is then detected. Detection of an increase in the $Ca^{2+}$ concentration relative to the reference specific $Ca^{2+}$ concentration associated with calcium channel activity of said polypeptide in the presence of the candidate agent indicates that the candidate agent is an agent which increases calcium channel activity. Detection of a decrease in the $Ca^{2+}$ concentration relative to the reference specific $Ca^{2+}$ concentration associated with calcium channel activity of said polypeptide in the presence of the candidate agent indicates that the candidate agent is an agent which decreases calcium channel activity. A preferred polypeptide comprising a calcium channel and a mutT domain is a polypeptide encoded by the nucleic acid of SEQ ID NO:5, having a sequence of amino acids as the sequence set forth in SEQ ID NO:6. In important embodiments, the ligand that associates with the mutT domain of a polypeptide comprising a calcium channel and a mutT domain is a nucleotide sugar. In preferred embodiments, the ligand that associates with the mutT domain of a polypeptide comprising a calcium channel and a mutT domain is ADP-ribose.

According to another aspect of the invention, a method for identifying an agent useful in modulating mutTCCH-1 hydrolase activity, is provided. The method involves (a) contacting a mutTCCH-1 polypeptide and a ligand that associates with a mutTCCH-1 polypeptide, in the presence or absence of a candidate agent suspected of modulating mutTCCH-1 hydrolase activity, (b) measuring mutTCCH-1 hydrolase activity, and (c) comparing the measured mutTCCH-1 hydrolase activity to a control to determine whether the candidate agent modulates mutTCCH-1 hydrolase activity. In some embodiments, the ligand that associates with a mutTCCH-1 polypeptide is a compound that contains a pyrophosphate linkage. In one embodiment, the ligand that associates with a mutTCCH-1 polypeptide is a compound that contains a dinucleoside linkage. In important embodiments, the ligand that associates with a mutTCCH-1 polypeptide is a nucleotide sugar. In preferred embodiments, the ligand that associates with a mutTCCH-1 polypeptide is ADP-ribose. In further embodiments, the ligand that associates with a mutTCCH-1 polypeptide is selected from the group consisting of ATP/deoxy-ATP, GTP/deoxy-GTP, deoxy-TTP, UTP, CTP/deoxy-CTP, UDP-galactose, UDP-mannose, UDP-xylose, UDP-glucose, UDP-glucNac, TDP-glucose, ADP-mannose, ADP-glucose, CDP-glycerol, CDP-choline, CDP-glucose, CDP-ethanolamine, ApnA (2 through 6), cyclic-ADP-ribose, NADH, NAD, NAADP, NADP, GDP-glucose, GDP-fucose, GDP-mannose, ApnA (n=2 through 6), cyclic-ADP-ribose, NADH, NAD, NADP, GDP-glucose, GDP-fucose, and GDP-mannose. In certain embodiments, the mutTCCH-1 polypeptide is encoded by a nucleic acid of SEQ ID NO:1. In preferred embodiments, the mutTCCH-1 polypeptide is the polypeptide of SEQ ID NO:2.

According to a further aspect of the invention, a method for identifying an agent useful in modulating calcium channel activity in a polypeptide comprising a calcium channel and a mutT domain, is provided. The method involves (a) contacting a polypeptide comprising a calcium channel and a mutT domain with a ligand that associates with the mutT domain of said polypeptide in the presence or absence of a candidate agent suspected of modulating calcium channel activity of the polypeptide, (b) measuring calcium channel activity of the polypeptide, and (c) comparing the measured calcium channel activity of the polypeptide to a control to determine whether the candidate agent modulates calcium channel activity of the polypeptide. In some embodiments, the polypeptide comprising a calcium channel and a mutT domain is a polypeptide encoded by the nucleic acid of SEQ ID NO:5, having a sequence of amino acids as the sequence set forth in SEQ ID NO:6. In certain embodiments, the ligand that associates with the mutT domain of a polypeptide comprising a calcium channel and a mutT domain is a compound that contains a pyrophosphate linkage. In one embodiment, the ligand that associates with the mutT domain of a polypeptide comprising a calcium channel and a mutT domain is a compound that contains a dinucleoside linkage. In important embodiments, the ligand that associates with the mutT domain of a polypeptide comprising a calcium channel and a mutT domain is a nucleotide sugar. In preferred embodiments, the ligand that associates with the mutT domain of a polypeptide comprising a calcium channel and a mutT domain is ADP-ribose. In further embodiments, the ligand that associates with the mutT domain of a polypeptide comprising a calcium channel and a mutT domain is selected from the group consisting of ATP/deoxy-ATP, GTP/deoxy-GTP, deoxy-TTP, UTP, CTP/deoxy-CTP, UDP-galactose, UDP-mannose, UDP-xylose, UDP-glucose, UDP-glucNac, TDP-glucose, ADP-mannose, ADP-glucose, CDP-glycerol, CDP-choline, CDP-glucose, CDP-ethanolamine, ApnA (2 through 6), cyclic-ADP-ribose, NADH, NAD, NAADP, NADP, GDP-glucose, GDP-fucose, GDP-mannose, ApnA (n=2 through 6), cyclic-ADP-ribose, NADH, NAD, NADP, GDP-glucose, GDP-fucose, and GDP-mannose.

The present invention thus involves, in several aspects, mutTCCH-1 polypeptides, isolated nucleic acids encoding those polypeptides, functional modifications and variants of the foregoing, useful fragments of the foregoing, as well as therapeutics and diagnostics relating thereto.

These and other objects of the invention will be described in further detail in connection with the detailed description of the invention.

BRIEF DESCRIPTION OF THE SEQUENCES

Figure 1A:
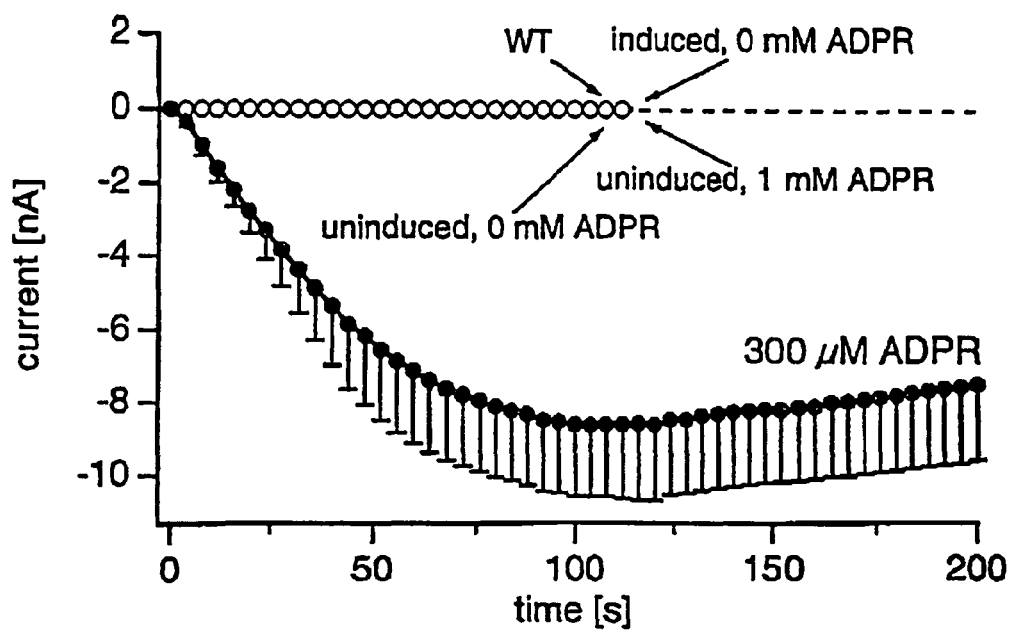
FIG. 1A is a graph illustrating the temporal development of averaged membrane currents at −80 mV under various experimental conditions.

SEQ ID NO:1 is the nucleotide sequence of the human mutTCCH-1 cDNA.

SEQ ID NO:2 is the predicted amino acid sequence of the translation product of human mutTCCH-1 cDNA (SEQ ID NO:1).

SEQ ID NO:3 is the nucleotide sequence of the human mutTCCH-1 cDNA encoding the polypeptide of SEQ ID NO:2.

SEQ ID NO:4 is the amino acid sequence of the consensus MutT domain.

SEQ ID NO:5 is the nucleotide sequence of the human putative $Ca^{2+}$ channel protein TrpC7 cDNA (GenBank Acc. Nos: AB001535 and NM_003307).

SEQ ID NO:6 is the predicted amino acid sequence of the translation product of the human putative $Ca^{2+}$ channel protein TrpC7 cDNA (SEQ ID NO:5).

SEQ ID NO:7 is the nucleotide sequence of a 5' PCR primer used in conjunction with the 3' PCR primer described in SEQ ID NO:8 to amplify TrpC7-specific gene sequences.

SEQ ID NO:8 is the nucleotide sequence of a 3' PCR primer used in conjunction with the 5' PCR primer described in SEQ ID NO:7 to amplify TrpC7-specific gene sequences.

SEQ ID NO:9 is the nucleotide sequence of a 5' PCR primer used in conjunction with the 3' PCR primer described in SEQ ID NO:10 to amplify mutTCCH-1-specific gene sequences.

SEQ ID NO:10 is the nucleotide sequence of a 3' PCR primer used in conjunction with the 5' PCR primer described in SEQ ID NO:9 to amplify mutTCCH-1-specific gene sequences.

SEQ ID NO:11 is the amino acid sequence of the FLAG epitope.

DETAILED DESCRIPTION OF THE INVENTION

One aspect of the invention involves the cloning of a cDNA encoding mutTCCH-1 (NUDT9). MutTCCH-1 according to the invention is an isolated nucleic acid molecule that comprises a nucleic acid molecule of SEQ ID NO:1, and codes for a polypeptide with hydrolase activity (phosphohydrolase and/or nucleotide sugar hydrolase). The sequence of the human mutTCCH-1 cDNA is presented as SEQ ID NO:1, and the predicted amino acid sequence of this cDNA's encoded protein product is presented as SEQ ID NO:2. MutTCCH-1 associated functions are believed to be mediated by mutTCCH-1's binding to other molecules and polypeptides. "MutTCCH-1 activity," or "mutTCCH-1 hydrolase" activity as used herein, refers to the recognition and subsequent hydrolysis by a mutTCCH-1 polypeptide of a pyrophosphate linkage and/or a sugar-phosphate linkage (also referred to herein as mutTCCH-1 pyrophosphohydrolase activity and/or mutTCCH-1 sugar-phosphate hydrolase activity). In general, pyrophosphohydrolase and/or sugar-phosphate hydrolase activity can be detected using assays well known in the art. For example, pyrophosphohydrolase activity towards a pyrophosphate-containing substrate (e.g., dATP, dGTP, PP-InsP$_5$), can be assayed as described in Safrany, S T et al., *EMBO J*, 1998, 17(22):6599-607, with its contents expressly incorporated herein by reference), using $^3$H-labeled substrates and HPLC (Safrany and Shears, *EMBO J*, 1998, 17(6): 1710-6), or gravity-fed ion-exchange columns (Shears et al., *J Biol Chem*, 1995, May 5; 270(18):10489-97) (See also under the Examples for the detection of nucleotide sugar hydrolase activity). TrpC7 pyrophosphohydrolase and/or sugar-phosphate hydrolase activity can also be detected using such conventional methods.

As used herein, a subject is a human, non-human primate, cow, horse, pig, sheep, goat, dog, cat or rodent. In all embodiments human mutTCCH-1 and human subjects are preferred.

The invention thus involves in one aspect an isolated mutTCCH-1 polypeptide, the cDNA encoding this polypeptide, functional modifications and variants of the foregoing, useful fragments of the foregoing, as well as diagnostics and therapeutics relating thereto.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulatable by standard techniques known to those of ordinary skill in the art.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

According to the invention, isolated nucleic acid molecules that code for a mutTCCH-1 polypeptide having hydrolase activity include: (a) nucleic acid molecules which hybridize under stringent conditions to a molecule consisting of a nucleic acid of SEQ ID NO:1 and which code for a mutTCCH-1 polypeptide having hydrolase activity, (b) deletions, additions and substitutions of (a) which code for a respective mutTCCH-1 polypeptide having hydrolase activity, (c) nucleic acid molecules that differ from the nucleic acid molecules of (a) or (b) in codon sequence due to the degeneracy of the genetic code, and (d) full-length complements of (a), (b) or (c). "Full-length," as used herein, refers to 100% complements of (a), (b) or (c).

Homologs and alleles of the mutTCCH-1 nucleic acids of the invention can be identified by conventional techniques. Thus, an aspect of the invention is those nucleic acid sequences which code for mutTCCH-1 polypeptides and which hybridize to a nucleic acid molecule consisting of the coding region of SEQ ID NO:1, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM NaH$_2$PO$_4$ (pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of mutTCCH-1 nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1 and SEQ ID NO:2, respectively, in some instances will share at least 50% nucleotide identity and/or at least 65% amino acid identity and in still other instances will share at least 60% nucleotide identity and/or at least 75% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://wwww.ncbi.nlm.nih.gov. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

In screening for mutTCCH-1 related genes, such as homologs and alleles of mutTCCH-1, a Southern blot may be performed using the foregoing conditions, together with a radioactive probe. After washing the membrane to which the DNA is finally transferred, the membrane can be placed against X-ray film or a phosphoimager plate to detect the radioactive signal.

Given the teachings herein of a full-length human mutTCCH-1 cDNA clone, other mammalian sequences such as the mouse cDNA clone corresponding to the human mutTCCH-1 gene can be isolated from a cDNA library, using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating mutTCCH-1 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1 or SEQ ID NO:3 or complements of thereof. A unique fragment is one that is a 'signature' for the larger nucleic acid. For example, the unique fragment is long enough to assure that its precise sequence is not found in molecules within the human genome outside of the mutTCCH-1 nucleic acids defined above (and human alleles). Those of ordinary skill in the art may apply no more than routine procedures to determine if a fragment is unique within the human genome. Unique fragments, however, exclude fragments completely composed of the nucleotide sequences of any of GenBank accession numbers listed in Table I, or other previously published sequences as of the filing date of this application.

A fragment which is completely composed of the sequence described in the foregoing GenBank deposits is one which does not include any of the nucleotides unique to the sequences of the invention. Thus, a unique fragment according to the invention must contain a nucleotide sequence other than the exact sequence of those in the GenBank deposits or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the mutTCCH-1 polypeptides, useful, for example, in the preparation of antibodies, immunoassays or therapeutic applications. Unique fragments further can be used as antisense molecules to inhibit the expression of mutTCCH-1 nucleic acids and polypeptides respectively.

As will be recognized by those skilled in the art, the size of the unique fragment will depend upon its conservancy in the genetic code. Thus, some regions of SEQ ID NO:1 or SEQ ID NO:3 and complements will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). Virtually any segment of the region of SEQ ID NO:1 beginning at nucleotide 1 and ending at nucleotide 1718, or SEQ ID NO:3 beginning at nucleotide 1 and ending at nucleotide 1050, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, the invention embraces antisense oligonucleotides that selectively bind to a nucleic acid molecule encoding a mutTCCH-1 polypeptide, to decrease mutTCCH-1 activity. When using antisense preparations of the invention, slow intravenous administration is preferred.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med.* 1(11):1116-1118, 1995). Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439-457, 1994) and at which proteins are not expected to bind. Finally, although, SEQ ID No:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1. Similarly, antisense to allelic or homologous mutTCCH-1 cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding mutTCCH-1 polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for mutTCCH-1 proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as *Escherichia coli* and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding mutTCCH-1 polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710-4716, 1996). Still another preferred expression vector is an adenovirus, described by Stratford-Perricaudet, which is defective for E1 and E3 proteins (*J. Clin. Invest.* 90:626-630, 1992). The use of the adenovirus as an Adeno.P1A recombinant is disclosed by Warnier et al., in intradermal injection in mice for immunization against P1A (*Int. J. Cancer*, 67:303-310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, mutTCCH-1 cDNA sequence containing expression vectors, to transfect host cells and cell lines, be these prokaryotic (e.g., *Escherichia coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells. The invention also permits the construction of mutTCCH-1 gene "knock-outs" in cells and in animals, providing materials for studying certain aspects of mutTCCH-1 activity.

The invention also provides isolated polypeptides (including whole proteins and partial proteins), encoded by the foregoing mutTCCH-1 nucleic acids, and include the polypeptide of SEQ ID NO:2 and unique fragments thereof. Such polypeptides are useful, for example, alone or as fusion proteins to hydrolyze nucleosides, to generate antibodies, as components of an immunoassay, etc. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of an mutTCCH-1 polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions or SEQ ID NO:2 will require longer segments to be unique while others will require only short segments, typically between 5 and 12 amino acids (e.g. 5, 6, 7, 8, 9, 10, 11 and 12 amino acids long or more, including each integer up to the full length, 350 amino acids long). Virtually any segment of SEQ ID NO:2, excluding the ones that share identity with it, that is 9 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, interaction with other molecules such as nucleoside triphosphates, nucleotide sugars, dinucleoside polyphosphates, etc. One important activity is the ability to act as a signature for identifying the polypeptide. Another is the ability to complex with HLA and to provoke in a human an immune response. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the mutTCCH-1 polypeptides described above. As used herein, a "variant" of a mutTCCH-1 polypeptide is a polypeptide which contains one or more modifications to the primary amino acid sequence of a mutTCCH-1 polypeptide. Modifications which create a mutTCCH-1 polypeptide variant are typically made to the nucleic acid which encodes the mutTCCH-1 polypeptide, and can include deletions, point mutations, truncations, amino acid substitutions and addition of amino acids or non-amino acid moieties to: 1) reduce or eliminate an activity of a mutTCCH-1 polypeptide; 2) enhance a property of a mutTCCH-1 polypeptide, such as protein stability in an expression system or the stability of protein-ligand binding; 3) provide a novel activity or property to a mutTCCH-1 polypeptide, such as addition of an antigenic epitope or addition of a detectable moiety; or 4) to provide equivalent or better binding to a mutTCCH-1 polypeptide receptor or other molecule (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the mutTCCH-1 amino acid sequence. One of skill in the art will be familiar with methods for predicting the effect on protein conformation of a change in protein sequence, and can thus "design" a variant mutTCCH-1 polypeptide according to known methods. One example of such a method is described by Dahiyat and Mayo in Science 278:82-87, 1997, whereby proteins can be designed de novo. The method can be applied to a known protein to vary only a portion of the polypeptide sequence. By applying the computational methods of Dahiyat and Mayo, specific variants of a MutT domain-containing polypeptide can be proposed and tested to determine whether the variant retains a desired conformation.

Variants can include mutTCCH-1 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a mutTCCH-1 polypeptide by eliminating proteolysis by proteases in an expression system (e.g., dibasic amino acid residues in yeast expression systems in which KEX2 protease activity is present).

Mutations of a nucleic acid which encodes a mutTCCH-1 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant mutTCCH-1 polypeptides) which are silent as to the amino acid sequence of the polypeptide, but which provide preferred codons for translation in a particular host. The preferred codons for translation of a nucleic acid in, e.g., *Escherichia coli*, are well known to those of ordinary skill in the art. Still other mutations can be made to the noncoding sequences of a mutTCCH-1 gene or cDNA clone to enhance expression of the polypeptide.

The skilled artisan will realize that conservative amino acid substitutions may be made in mutTCCH-1 polypeptides to provide functionally equivalent variants of the foregoing polypeptides, i.e, the variants retain the functional capabilities of the mutTCCH-1 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the mutTCCH-1 polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of mutTCCH-1 polypeptides, i.e., variants of mutTCCH-1 polypeptides which retain the function of the natural mutTCCH-1 polypeptides, are contemplated by the invention. Conservative amino-acid substitutions in the amino acid sequence of mutTCCH-1 polypeptides to produce functionally equivalent variants of mutTCCH-1 polypeptides typically are made by alteration of a nucleic acid encoding mutTCCH-1 polypeptides (SEQ ID NOs:1, 3). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a mutTCCH-1 polypeptide. The activity of functionally equivalent fragments of mutTCCH-1 polypeptides can be tested by cloning the gene encoding the altered mutTCCH-1 polypeptide into a bacterial or mammalian expression vector, introducing the vector into an appropriate host cell, expressing the altered mutTCCH-1 polypeptide, and testing for a functional capability of the mutTCCH-1 polypeptides as disclosed herein (e.g., pyrophosphohydrolyzing activity, etc.).

The invention as described herein has a number of uses, some of which are described elsewhere herein. First, the invention permits isolation of mutTCCH-1 polypeptides. A variety of methodologies well-known to the skilled practitioner can be utilized to obtain isolated mutTCCH-1 molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mutTCCH-1 mRNA in cell-free extracts such as the reticulocyte lysate system also may be used to produce mutTCCH-1 polypeptides. Those skilled in the art also can readily follow known methods for isolating mutTCCH-1 polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from mutTCCH-1 polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and use standard mutagenesis techniques to create one or more dominant negative variant polypeptides. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The isolation of the mutTCCH-1 cDNA also makes it possible for the artisan to diagnose a disorder characterized by an aberrant expression of mutTCCH-1. These methods involve determining expression of the mutTCCH-1 gene, and/or mutTCCH-1 polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted mutTCCH-1 protein.

The invention also embraces isolated peptide binding agents which, for example, can be antibodies or fragments of antibodies ("binding polypeptides"), having the ability to selectively bind to mutTCCH-1 polypeptides. Antibodies include polyclonal and monoclonal antibodies, prepared according to conventional methodology. In certain embodiments, the invention excludes binding agents (e.g., antibodies) that bind to the polypeptides encoded by the nucleic acids of Table I.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to mutTCCH-1 polypeptides, and complexes of both mutTCCH-1 polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the mutTCCH-1 polypeptide or a complex of mutTCCH-1 and a binding partner. This process can be repeated through several cycles of reselection of phage that bind to the mutTCCH-1 polypeptide or complex. Repeated rounds lead to enrichment of phage bearing particular sequences. DNA sequence analysis can be conducted to identify the sequences of the expressed polypeptides. The minimal linear portion of the sequence that binds to the mutTCCH-1 polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the mutTCCH-1 polypeptides. Thus, the mutTCCH-1 polypeptides of the invention, or a fragment thereof, or complexes of mutTCCH-1 and a binding partner can be used to screen peptide libraries, including phage display libraries, to identify and select peptide binding partners of the mutTCCH-1 polypeptides of the invention. Such molecules can be used, as described, for screening assays, for purification protocols, for interfering directly with the functioning of mutTCCH-1 and for other purposes that will be apparent to those of ordinary skill in the art.

A mutTCCH-1 polypeptide, or a fragment thereof, also can be used to isolate their native binding partners. Isolation of binding partners may be performed according to well-known methods. For example, isolated mutTCCH-1 polypeptides (that include mutTCCH-1 phosphorylated polypeptides) can be attached to a substrate, and then a solution suspected of containing an mutTCCH-1 binding partner may be applied to the substrate. If the binding partner for mutTCCH-1 polypeptides is present in the solution, then it will bind to the substrate-bound mutTCCH-1 polypeptide. The binding partner then may be isolated. Other proteins which are binding partners for mutTCCH-1, may be isolated by similar methods without undue experimentation.

The invention also provides methods to measure the level of mutTCCH-1 expression in a subject. This can be performed by first obtaining a test sample from the subject. The test sample can be tissue or biological fluid. Tissues include brain, heart, serum, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. In certain embodiments, test samples originate from colon, breast and prostate tissues, and biological fluids include blood, saliva and urine. Both invasive and non-invasive techniques can be used to obtain such samples and are well documented in the art. At the molecular level both PCR and Northern blotting can be used to determine the level of mutTCCH-1 mRNA using products of this invention described earlier, and protocols well known in the art that are found in references which compile such methods. At the protein level, mutTCCH-1 expression can be determined using either polyclonal or monoclonal anti-mutTCCH-1 sera in combination with standard immunological assays. The preferred methods will compare the measured level of mutTCCH-1 expression of the test sample to a control. A control can include a known amount of a nucleic acid probe, a mutTCCH-1 epitope (such as a mutTCCH-1 expression product), or a similar test sample of a subject with a control or 'normal' level of mutTCCH-1 expression.

The invention also embraces a method for treating subjects expressing a mutant mutTCCH-1. It involves first determining whether the subject, and in particular a specific tissue or fluid of the subject, expresses a mutant mutTCCH-1 or a wild-type mutTCCH-1. As used herein, "wild-type" refers generally to a molecule which is ordinary, common, without defect or affect, and not mutant. An ordinary molecule, also refers generally to sequences or structures that, while they may vary from a canonical sequence or structure, comprise neutral polymorphisms and do not vary in function from a molecule having a non-mutant sequence or structure. According to the invention, a wild-type mutTCCH-1 is, for example, a nucleic acid of SEQ ID NO:1 and its encoded polypeptide presented as SEQ ID NO:2). Wild-type mutTCCH-1 is capable of binding, for example, to dATP. Conversely, a "mutant" mutTCCH-1 typically has undergone a nucleic acid substitution that results in a non-conservative amino acid substitution at the polypeptide level that changes the mutTCCH-1's binding characteristics, thus inducing, for example, apoptosis in the cell.

The mode of administration and dosage of the therapeutic agent of the invention will vary with the particular stage of the condition being treated, the age and physical condition of the subject being treated, the duration of the treatment, the nature of the concurrent therapy (if any), the specific route of administration, and the like factors within the knowledge and expertise of the health practioner.

MutTCCH-1 polypeptides preferably are produced recombinantly, although such polypeptides may be isolated from biological extracts. Recombinantly produced mutTCCH-1 polypeptides include chimeric proteins comprising a fusion of a mutTCCH-1 protein with another polypeptide, e.g., a polypeptide capable of providing or enhancing protein-protein binding, sequence specific nucleic acid binding (such as GAL4), enhancing stability of the mutTCCH-1 polypeptide under assay conditions, or providing a detectable moiety, such as green fluorescent protein. A polypeptide fused to a mutTCCH-1 polypeptide or fragment may also provide means of readily detecting the fusion protein, e.g., by immunological recognition or by fluorescent labeling.

The invention also is useful in the generation of transgenic non-human animals. As used herein, "transgenic non-human animals" includes non-human animals having one or more exogenous nucleic acid molecules incorporated in germ line cells and/or somatic cells. Thus the transgenic animals include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to mutTCCH-1 nucleic acid molecules to increase expression of mutTCCH-1 in a regulated or conditional manner. Trans-acting negative regulators of mutTCCH-1 activity or expression also can be operably linked to a conditional promoter as described above. Such trans-acting regulators include antisense mutTCCH-1 nucleic acids molecules, nucleic acid molecules which encode dominant negative mutTCCH-1 molecules, ribozyme molecules specific for mutTCCH-1 nucleic acids, and the like. The transgenic non-human animals are useful in experiments directed toward testing biochemical or physiological effects of diagnostics or therapeutics for conditions characterized by increased or decreased mutTCCH-1 expression. Other uses will be apparent to one of ordinary skill in the art.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of identifying agents or lead compounds for agents active at the level of a mutTCCH-1 or mutTCCH-1 fragment dependent cellular function. In particular, such functions include interaction with other polypeptides or fragments thereof, interaction with other molecules such as nucleoside triphosphates, nucleotide sugars, dinucleoside polyphosphates, etc. Generally, the screening methods involve assaying for compounds which interfere with mutTCCH-1 activity (such as mutTCCH-1 phosphohydrolyzing), although compounds which enhance mutTCCH-1 activity also can be assayed using the screening methods. Such methods are adaptable to automated, high throughput screening of compounds. The target therapeutic indications for pharmacological agents detected by the screening methods are limited only in that the target cellular function be subject to modulation by alteration of the formation of a complex comprising a mutTCCH-1 polypeptide or fragment thereof and one or more natural mutTCCH-1 binding targets, such as a phosphate bond, etc. Target indications include cellular processes modulated by mutTCCH-1 such as nucleoside catabolism, and affected by mutTCCH-1's ability to form complexes with other molecules and polypeptides.

A wide variety of assays for pharmacological agents are provided, including, labeled in vitro protein-ligand binding assays, electrophoretic mobility shift assays, immunoassays, cell-based assays such as two- or three-hybrid screens, expression assays, etc. For example, two-hybrid screens are used to rapidly examine the effect of transfected nucleic acids on the intracellular binding of mutTCCH-1 or mutTCCH-1 fragments to specific intracellular targets (e.g. a nucleoside). The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a mutTCCH-1 polypeptide fused to a GAL4 DNA binding domain and a nucleic acid encoding a reporter gene operably linked to a gene expression regulatory region, such as one or more GAL4 binding sites. Activation of reporter gene transcription occurs when the mutTCCH-1 and reporter fusion polypeptides bind such as to enable transcription of the reporter gene. Agents which modulate a mutTCCH-1 polypeptide mediated cell function are then detected through a change in the expression of reporter gene. Methods for determining changes in the expression of a reporter gene are known in the art.

MutTCCH-1 fragments used in the methods, when not produced by a transfected nucleic acid are added to an assay mixture as an isolated polypeptide. MutTCCH-1 polypeptides preferably are produced recombinantly, although such polypeptides may be isolated from biological extracts. Recombinantly produced mutTCCH-1 polypeptides include chimeric proteins comprising a fusion of a mutTCCH-1 protein with another polypeptide, e.g., a polypeptide capable of providing or enhancing protein-protein binding, sequence specific nucleic acid binding (such as GAL4), enhancing stability of the mutTCCH-1 polypeptide under assay conditions, or providing a detectable moiety, such as green fluorescent protein or Flag epitope.

The assay mixture is comprised of a natural intracellular mutTCCH-1 binding target capable of interacting with mutTCCH-1. While natural mutTCCH-1 binding targets may be used, it is frequently preferred to use portions (e.g., peptides or nucleic acid fragments) or analogs (i.e., agents which mimic the mutTCCH-1 binding properties of the natural binding target for purposes of the assay) of the mutTCCH-1 binding target so long as the portion or analog provides binding affinity and avidity to the mutTCCH-1 fragment measurable in the assay.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate pharmacological agent, the mutTCCH-1 polypeptide specifically binds the cellular binding target (i.e., a pyrophosphate linkage containing molecule), a portion thereof or analog thereof. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the mutTCCH-1 polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein; etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of mutTCCH-1 polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseseradish peroxidase, etc.). The label may be bound to a mutTCCH-1 binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides mutTCCH-1-specific binding agents, methods of identifying and making such agents, and their use in diagnosis, therapy and pharmaceutical development. For example, mutTCCH-1-specific pharmacological agents are useful in a variety of diagnostic and therapeutic applications, especially where disease or disease prognosis is associated with altered mutTCCH-1 binding characteristics. Novel mutTCCH-1-specific binding agents include mutTCCH-1-specific antibodies, cell surface receptors, and other natural intracellular and extracellular binding agents identified with assays such as two hybrid screens, and non-natural intracellular and extracellular binding agents identified in screens of chemical libraries and the like.

In general, the specificity of mutTCCH-1 binding to a specific molecule is determined by binding equilibrium constants. Targets which are capable of selectively binding a mutTCCH-1 polypeptide preferably have binding equilibrium constants of at least about $10^7$ $M^{-1}$ more preferably at least about $10^8$ $M^{-1}$, and most preferably at least about $10^9$ $M^{-1}$. The wide variety of cell based and cell free assays may be used to demonstrate mutTCCH-1-specific binding. Cell based assays include one, two and three hybrid screens, assays in which mutTCCH-1-mediated transcription is inhibited or increased, etc. Cell free assays include mutTCCH-1-protein binding assays, immunoassays, etc. Other assays useful for screening agents which bind mutTCCH-1 polypeptides include fluorescence resonance energy transfer (FRET), and electrophoretic mobility shift analysis (EMSA).

According to a further aspect of the invention, a method for identifying an agent useful in modulating calcium channel activity in a polypeptide comprising a calcium channel and a mutT domain, is provided. The method involves (a) contacting a polypeptide comprising a calcium channel and a mutT domain with a ligand that associates with the mutT domain of said polypeptide in the presence or absence of a candidate agent suspected of modulating calcium channel activity of the polypeptide, (b) measuring calcium channel activity of the polypeptide, and (c) comparing the measured calcium channel activity of the polypeptide to a control to determine whether the candidate agent modulates calcium channel activity of the polypeptide. It is to be understood that a mutT domain may be different to the one depicted in SEQ ID NO:4. In certain embodiments, the mutT domain is that described for TrpC7 (see SEQ ID NO:6).

As used herein, "calcium channel activity" refers to $Ca^{2+}$ transport ("$Ca^{2+}$ fluxing") across the plasma membrane (of a cell) that is mediated by a calcium channel polypeptide, including TrpC7 (SEQ ID NO:6). The calcium channel polypeptide typically has one or more of the following properties: high selectivity, a unitary conductance below the detection level of the patch clamp method, and is subject to inhibition by high intracellular calcium levels. Such activity can be easily detected using standard methodology well known in the art. See, e.g., the Examples and Neher, E., "Ion channels for communication between and within cells", *Science*, 1992; 256:498-502; and Hoth, M., and Penner, R., "Depletion of intracellular calcium stores activates a calcium current in mast cells", *Nature*, 1992; 355 (6358):353-6. As mentioned elsewhere, the transport of ions other than calcium, e.g. Mg, Zn, Sr, Mn, can also be measured/detected within the meaning and scope of the present invention.

One of ordinary skill in the art can easily identify a proper control to use when comparing such calcium channel activities. A control calcium channel activity, for example, is the calcium channel activity of a polypeptide comprising a calcium channel and a mutT domain in the presence of a ligand that associates with the mutT domain of said polypeptide, but in the absence of a candidate agent suspected of modulating calcium channel activity of the polypeptide.

Generally, the screening methods involve assaying for compounds which modulate calcium channel activity through the mutT domain of a polypeptide comprising a calcium channel and a mutT domain. Thus, agents useful in modulating mutTCCH-1 activity, as described above, are also useful in this aspect of the invention (e.g., as agents useful in the modulation of calcium channel activity).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention will be more fully understood by reference to the following examples. These examples, however, are merely intended to illustrate the embodiments of the invention and are not to be construed to limit the scope of the invention.

Examples

As part of a broad approach for identifying proteins involved in calcium regulation in the immune system, we have cloned genes that are homologous to one or more known types of calcium channels expressed in immune system cells or tissues. Using this approach with the TrpC7 putative calcium channel sequence (Nagamine, K., et al., *Genomics*, 1998, 54:124-31), we identified and cloned a novel cDNA from a spleen cDNA library, which we subsequently designated NUDT9 (mutTCCH-1).

Experimental Procedures
Materials and Methods
RT-PCR Analysis of Expression

For analysis of TrpC7 expression, the oligos used were cagtgtggctacacgcatga (SEQ ID NO:7) and tcaggcccgtgaagacgatg (SEQ ID NO:8) to produce a 138 bp band. For analysis of NUDT9 expression, the oligos used were ggcaagactataagcctgtg (SEQ ID NO:9) and ataatgggatctgcagcgtg (SEQ ID NO:10) to produce a 252 bp band. Amplification conditions used were 95 degree melting, 55 degree annealing, and 72 degree extension for 25 cycles. All libraries screened were from Life Technologies.

Cloning and Sequence Analysis of TrpC7 and NUDT9

The genetrapper II solution hybridization method (Life Technologies) was used to isolate both TrpC7 and NUDT9 cDNAs. For TrpC7, five PCR positive colonies were obtained from the leukocyte library that was positive for TrpC7 expression by RT-PCR, and the longest of these (4.0 kb) was sequenced. For NUDT9, 35 colonies were obtained from the spleen library, which was positive for NUDT9 expression. Eight of these were end-sequenced to confirm that they represented the same transcript and one was fully sequenced in both directions.

Construction of a FLAG-Tagged TrpC7 Expression Construct

Brain cDNA was purchased from Clontech and used to obtain by RT-PCR the TrpC7 coding sequence not present in the 4.0 kb fragment isolated by cDNA cloning. This sequence extended from the internal NotI site present in TrpC7 to the stop codon, and included an additional KpnI site just internal to the stop codon, thereby adding an additional two amino acids (glycine and threonine) to the 3' end of TrpC7, followed by a stop codon and a SpeI site just beyond the stop codon. This RT-PCR fragment was ligated onto the 4.0 Kb cDNA using the NotI site and SpeI sites, producing a full length TrpC7 coding sequence. The internal NotI site in this full length TrpC7 template was then removed by site-directed mutagenesis, and PCR was used to generate a TrpC7 expression construct containing a NotI site at the 5' end internal to the initiating methionine. This construct was subcloned into a modified pcDNA4/TO vector containing a Kozak sequence, initiating methionine, FLAG tag, and polylinker including a NotI site in appropriate frame with the FLAG tag and a 3' SpeI site. This produced an expression plasmid which produced a protein with the following predicted sequence: MGDYKD-DDDKRPLA-(SEQ ID NO:11) followed by the TrpC7 coding sequence beginning at amino acid 3 and extending to amino acid 1503—followed by GT and then the stop codon. Sequencing of the full-length TrpC7 construct showed four single base pair differences with the original TrpC7 sequence. Three of these did not change the predicted amino acid sequence, while the fourth introduced a glycine for serine substitution at amino acid 1367 relative to the published TrpC7 sequence. This was interpreted as a possible polymorphic form of TrpC7, therefore an otherwise identical wild type TrpC7 expression construct was also produced. FLAG-TrpC7 and FLAG-TrpC7 (S1367G) constructs were used in each of the various types of experiments presented, and were indistinguishable in terms of their biochemical and biophysical behavior.

Construction of E. Coli Expression Constructs for NUDT9, and the NUDT9 Homology Region of TrpC7

A full-length coding sequence for NUDT9 was produced by PCR so as to place an NcoI site at the 5' end and a NotI site at the 3' end, and subcloned into the pET-24d T7 expression vector from Novagen. For the TrpC7 NUDT9 homology region, a construct was made by PCR to include an NcoI site, an artificial start codon, amino acids 1197-1503, a stop codon, and a 3' NotI site. This was also subcloned into pET-24d. Both a wild type TrpC7 NUDT9 homology region and an S1367G TrpC7 NUDT9 homology region construct were evaluated and were indistinguishable in terms of enzymatic activity in vitro.

E. Coli Expression and Purification of NUDT9, and of the NUDT9 Homology Region of TrpC7

BL21 (DE3) cells containing the respective expression plasmids were grown at 37° C. in LB broth on a shaker to an A600 of about 0.6 and induced by the addition of isopropyl-β-D-thiogalactopyranoside to a concentration of 1 mM. The cells were allowed to grow for an additional 4 h, harvested, washed by suspension in isotonic saline, centrifuged in pre-weighed centrifuge tubes, and the packed cells were stored at −80° C. The expressed protein leaked out of the frozen and thawed cells merely by washing them in 50 mM Tris, pH 7.5, 1 mM EDTA, 0.1 mM dithiothreitol. Most endogenous proteins remained within the cells resulting in an extract enriched for the expressed enzymes. In the case of NUDT9, enzyme was extracted in the freeze-thaw fraction and ammonium sulfate was added to 35% final concentration. The precipitate was discarded after centrifugation and ammonium sulfate was added to the supernatant to a final concentration of 50%. The precipitate was collected by centrifugation, dissolved then chromatographed, then chromatographed on a gel filtration column (Sephadex G-100). The active fractions containing the majority of the enzyme were pooled, concentrated by centrifugation in an Amicon Centriprep30, dialyzed and chromatographed on DEAE-sepharose. The purified enzyme was then concentrated from the pooled active fractions again using an Amicon Centriprep30. For the NUDT9 homology region of TrpC7 (both published and S1367G versions), the protein was extracted in the freeze-thaw fraction and ammonium sulfate was added to 35% final concentration and centrifuged. The precipitate was dissolved, dialyzed and chromatographed on DEAE-sepharose. The purified enzyme was concentrated from the pooled active fractions by precipitation with 70% ammonium sulfate.

Assays for Nudix Type Activity of NUDT9, and the NUDT9 Homology Region of TrpC7

Enzyme Assay—Enzyme velocities were quantified by measuring the conversion of a phosphatase-insensitive substrate, ADP-ribose, to the phosphatase-sensitive products, AMP and ribose-5-phosphate. The liberated inorganic orthophosphate was measured by the procedure of Ames and Dubin (Ames, B. N., and Dubin, D. T., J. Biol. Chem. 1960, 235:769-775). The standard incubation mixture (50 μl) contained 50 mM Tris-Cl, pH 9.0, 16 mM $MgCl_2$, 2 mM ADP-ribose, 0.2-1 milliunits of enzyme and 4 units of alkaline intestinal phosphatase. After 30 min at 37° C., the reaction was terminated by the addition of EDTA and inorganic orthophosphate was measured. A unit of enzyme hydrolyzes 1 μmol of substrate per min under these conditions. Note that 2 moles of phosphate are liberated per mole of ADP-ribose hydrolyzed.

Product determination—The standard assay mixture (minus alkaline intestinal phosphatase) was incubated 30 min at 37° C. and terminated by the addition of 50 μl of a mixture of four parts of Norit (20% packed volume) and one part of 7% $HClO_4$ to remove adenine containing nucleotides. After centrifugation, 50 μl was adjusted to an alkaline pH and incubated for an additional 30 min at 37° C. with alkaline intestinal phosphatase to hydrolyze the ribose-5-phosphate formed. The subsequent free phosphate was measured and compared to a control reaction that did not undergo Norit treatment. The stoichiometric relation between the two suggests the products are AMP and ribose-5-phosphate.

Construction of HEK293 Cells Expressing Tetracycline Regulated TrpC7

FLAG-TrpC7 and FLAG-TrpC7 (S1367G) constructs in pcDNA4/T0 was electroporated into HEK293 cells previously transfected with the pcDNA6/TR construct so as to express the tetracycline repressor protein. Cells placed under zeocin selection, and zeocin resistant clones were screened for inducible expression of a FLAG-tagged protein of the correct molecular weight. After treatment or not for 24 hours with 1 μg/ml of tetracycline, $10^6$ cells were analyzed for expression of a FLAG-reactive protein by anti-FLAG immunoprecipitation/anti-FLAG immunoblotting. Several clones were used in subsequent analyses, and all exhibited indistinguishable biochemical and biophysical behavior. The clones with the lowest level of basal expression and the best overall level of protein expression after tetracycline or doxycycline treatment were chosen for further analysis.

SDS/PAGE, Immunoprecipitation, Immunblotting and Immunofluorescence

HEK-293 cells with inducible expression of FLAG-TrpC7 were left untreated or were treated with tetracycline. After 24 hours, the cells were fixed and analyzed by anti-FLAG immunofluorescence staining. In the absence of tetracycline, there is no detectable FLAG-reactive staining. These were all performed using standard methods. Anti-FLAG antibody was purchased from IBI-Kodak.

Cell Culture

Wild type and tetracycline-inducible HEK293 FLAG-TrpC7 expressing cells were cultured at 37° C./5% $CO_2$ in DMEM supplemented with 10% FBS and 2 mM glutamine. The medium was supplemented with blasticidin (5 µg/ml; Invitrogen) and zeocin (0.4 mg/ml; Invitrogen). Cells were resuspended in media containing 1 µg/ml tetracycline (Invitrogen) 24 hours before patch-clamp experiments.

Electrophysiology

For patch-clamp experiments, coverslips were transferred to the recording chamber and kept in a standard modified Ringer's solution of the following composition (in mM): NaCl 145, KCl 2.8, $CaCl_2$ 1, $MgCl_2$ 2, glucose 10, Hepes-NaOH 10, pH 7.2. Intracellular pipette-filling solutions contained (in mM): Cs-glutamate 145, NaCl 8, $MgCl_2$ 1, Cs-BAPTA 10, pH 7.2 adjusted with CsOH. Adenosine 5-diphospho (ADP)-ribose, cyclic ADP-Ribose, guanosine 5-diphospho (GDP)-glucose, GDP-mannose, uridine diphospho (UDP)-glucose, UDP-mannose, ADP-glucose, ADP-mannose, cytosine diphospho (CDP)-glucose, ribose-5-phosphate, adenosine 5-monophosphate (AMP), nicotinamide adenine dinucleotide (NAD) and inositol 1,4,5-trisphosphate ($InsP_3$) were purchased from Sigma. The agonists were dissolved in the standard intracellular solution. Ionomycin (Sigma) was added to the extracellular standard solution.

Patch-clamp experiments were performed in the tight-seal whole-cell configuration at 21-25° C. High-resolution current recordings were acquired by a computer-based patch-clamp amplifier system (EPC-9, HEKA, Lambrecht, Germany). Sylgard-coated patch pipettes had resistances between 2-4 MΩ after filling with the standard intracellular solution. Immediately following establishment of the whole-cell configuration, voltage ramps of 50 ms duration spanning the voltage range of −100 to +100 mV were delivered from a holding potential of 0 mV at a rate of 0.5 Hz over a period of 200 to 400 seconds. All voltages were corrected for a liquid junction potential of 10 mV between external and internal solutions. Currents were filtered at 2.9 kHz and digitized at 100 µs intervals. Capacitive currents and series resistance were determined and corrected before each voltage ramp using the automatic capacitance compensation of the EPC-9. For analysis, the very first ramps were digitally filtered at 2 kHz, pooled and used for leak-subtraction of all subsequent current records. The low-resolution temporal development of currents at a given potential was extracted from the leak-corrected individual ramp current records by measuring the current amplitudes at voltages of −80 mV or +80 mV.

Results and Discussion

TrpC7 is putative calcium channel sequence (Nagamine, K., et al., *Genomics*, 1998, 54:124-31), belonging to a family of proteins that includes MLSN-1, MTR-1, and the *C. elegans* proteins C05C12.3, T01H8.5, and F54D1.5. This family of proteins (which we term the *C. elegans* Channel Homologue or CeCH family) has a characteristic 600-700 amino acid region (Amino Terminal Unique region or ATU) which can be divided into four smaller subregions based on the presence of poorly conserved intervening sequences in one or more family members. The ATU is followed by a short region with high homology between Trp and CeCH family proteins, and then an approximately 300 amino acid region which contains the putative TM (transmembrane) spans. Downstream from the TM spans is a region with high predicted coiled character and then a carboxy terminal extension of highly variable length and structure.

As part of a broad approach for identifying proteins involved in calcium regulation in the immune system, we have cloned genes that are homologous to one or more known types of calcium channels expressed in immune system cells or tissues. Using this approach with the TrpC7 putative calcium channel sequence (Nagamine, K., et al., *Genomics*, 1998, 54:124-31), we identified and cloned a novel cDNA from a spleen cDNA library, which we subsequently designated NUDT9. By RT-PCR analysis, NUDT9 is widely expressed and is present in most, but not all, tissues in which TrpC7 is expressed. It is homologous only to the C-terminal region of TrpC7 and in addition to a *C. elegans* predicted protein EEED8.8. Sequence analysis of NUDT9 revealed the presence of a putative signal peptide/anchor and a Nudix box sequence motif (see SEQ ID NOs: 2 and 6). Nudix boxes are found in a diverse family of enzymes catalyzing the hydrolysis of nucleoside diphosphate derivatives (Bessman, M. J., et al., *J Biol Chem*, 1996, 271:25059-62). This motif is highly conserved in EEED8.8, and is present in a less conserved form in the TrpC7 NUDT9 homology region.

ClustalW alignment of the NUDT9 homology region of TrpC7, EEED8.8, and NUDT9 revealed the presence of the RIL and QE amino acids present in TrpC7 in place of the conserved REF triad and EE diad found in NUDT9 and EEED8.8. The REF triad is found in many mutT proteins, and the EE diad is required for activity of the bacterial mutT protein (Lin, J., et al., *Biochemistry*, 1996, 35:6715-26), and it is likely that these substitutions in TrpC7 account in large part for the decreased activity of the TrpC7 NUDT9 homology region (see discussion below).

Based on the presence of the nudix box (SEQ ID NO:4) in NUDT9 and the homology between NUDT9 and TrpC7, we surmised that identifying a potential substrate for NUDT9 would provide insight into TrpC7 function. Therefore, we expressed NUDT9 in *E. coli*, purified the protein, and screened a series of potential nucleoside diphosphate derivatives. Substrates tested were: ADP-ribose ATP/deoxy-ATP, GTP/deoxy-GTP, deoxy-TTP, UTP, CTP/deoxy-CTP, UDP-galactose, UDP-mannose, UDP-xylose, UDP-glucose, UDP-glucNac, TDP-glucose, ADP-mannose, ADP-glucose, CDP-glycerol, CDP-choline, CDP-glucose, CDP-ethanolamine, ApnA (2 through 6), cyclic-ADP-ribose, NADH, NAD, NAADP, NADP, GDP-glucose, GDP-fucose, GDP-mannose, ApnA (n=2 through 6), cyclic-ADP-ribose, NADH, NAD, NADP, GDP-glucose, GDP-fucose, GDP-mannose. $K_m$ and $V_{max}$ were calculated by non-linear regression analysis of Lineweaver-Burke plots. The recombinant protein was found to be a highly specific ADP-ribose pyrophosphatase (hydrolase), yielding AMP and ribose-5-phosphate as products. We also expressed the TrpC7 NUDT9 homology region in *E. coli* and evaluated its activity towards the same panel of substrates. The TrpC7 NUDT9 homology region had a similar specificity for ADP-ribose, but with a far lower specific activity (Vmax_0.1 µmol/min/mg protein, approximately 1% of the activity observed for NUDT9).

The simplest model for relating NUDT9 activity to TrpC7 function is that ADP-ribose is involved in channel gating by TrpC7. To test this, we utilized HEK293 cell lines with tetracycline-regulated expression of FLAG-tagged TrpC7 (see methods). After tetracycline induction, substantial expression of anti-FLAG immunoreactive protein of the correct predicted molecular weight was detected by western blotting. In addition, anti-FLAG immunofluorescence analysis indicated that the induced FLAG-TrpC7 was detected peripherally, consistent with a significant portion of FLAG-TrpC7 being localized at or near the plasma membrane.

Figure 1B:
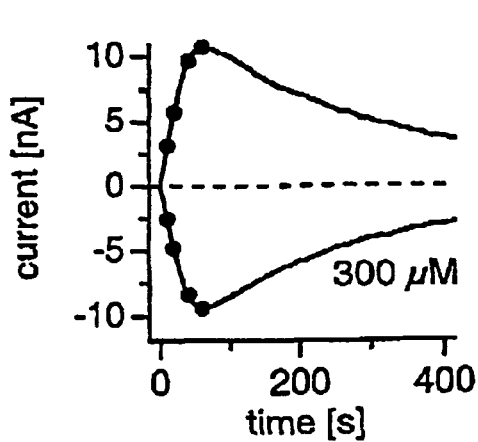
FIGS. 1B and 1C are graphs illustrating that ADP-ribose induces cationic currents when FLAG-TrpC7 is expressed.
Figure 1C:
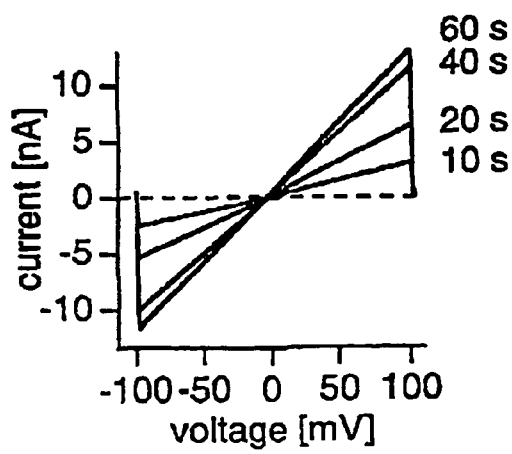

Based on the localization of a portion of the expressed FLAG-TrpC7 in proximity to the plasma membrane, we performed patch-clamp analyses of plasma membrane currents with or without tetracycline treatment, and with or without ADP-ribose present in the patch pipette (FIGS. 1A, 1B and 1C). Without tetracycline induction, ADP-ribose has no detectable effect on plasma membrane currents (FIG. 1A). Furthermore, in the absence of ADP-ribose in the patch pipette, basal currents in tetracycline treated cells are essentially the same in form and magnitude as wild type HEK293 cells, suggesting that TrpC7 is not open to a detectable extent under conditions established by our standard intracellular solutions. In contrast, after tetracycline induction, extremely large currents are induced by 100 µM ADP-ribose (FIGS. 1A, 1B and 1C), but not by any other closely related molecules, including NAD, cyclic ADP-ribose, ADP-glucose, ADP-mannose, GDP-glucose, GDP-mannose, UDP-glucose, and UDP-mannose. At 100 µM, no detectable gating was detected with any of these compounds, nor with 20 µM inositol-1,4,5-trisphosphate or 10 µM ionomycin. Together, these data demonstrate that TrpC7 is not a store-operated channel, but is highly specifically gated by intracellular ADP-ribose.

Figure 2A:
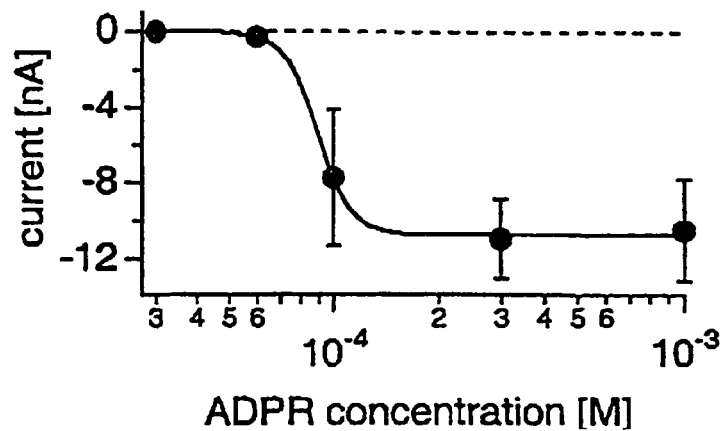
FIG. 2A is a dose-response curve for ADP-ribose-dependent gating of TrpC7.
Figure 2B:
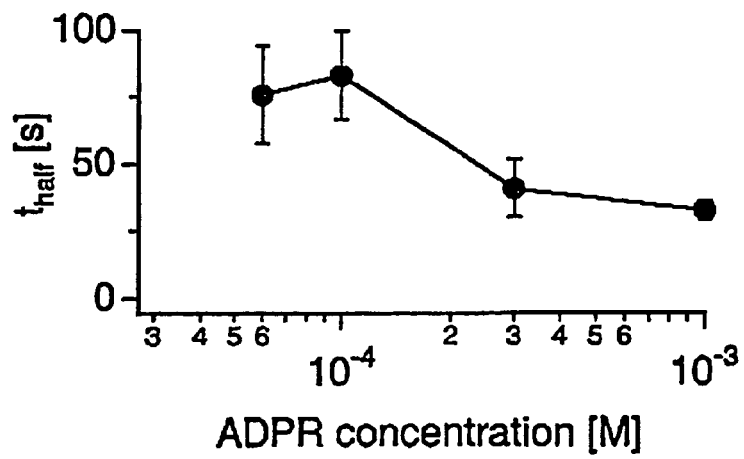
FIG. 2B is a graph showing the kinetics of ADP-ribose-dependent gating of TrpC7.
Figure 2C:
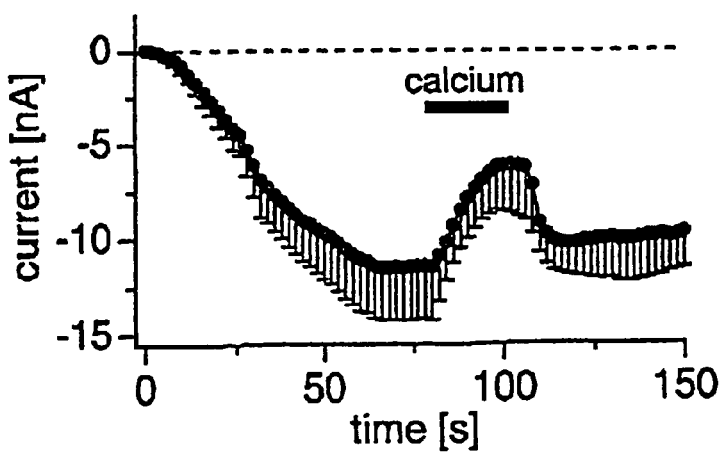
FIG. 2C is a graph illustrating that TrpC7 is permeable to calcium.

A limited investigation of the gating characteristics and nature of the currents carried by TrpC7 is shown in (FIG. 2). The relationship between [ADP-ribose]$_i$ and current magnitude or latency of current development are presented in FIGS. 2A and 2B, respectively. Both analyses indicate that TrpC7 activation begins to occur at around 60-100 µLM ADP-ribose and saturates around 300 µM, indicating a very steep dose-response relationship. Such a threshold behavior for ADP-ribose gating of TrpC7 might result from a high degree of agonist cooperativity or intracellular metabolism or high-affinity binding/buffering of ADP-ribose that need to be overcome before channels are gated. Analyses of ADP-ribose induced currents in isotonic saline or isotonic calcium are presented in FIG. 2C. The ability of isotonic calcium to maintain approximately 50% of the current observed in isotonic saline indicates that FLAG-TrpC7 is highly permeable for calcium and would carry a significant fraction of calcium under physiologic conditions. Calcium permeation is likely to account for the slight outward rectification observed in the I/V plots of FIGS. 1B and 1C and may also be responsible for the secondary "inactivation" of currents seen in FIGS. 1A, 1B, and 1C.

In summary, we have identified NUDT9 as a highly specific Nudix hydrolase active on ADP-ribose and demonstrated that the TrpC7 protein, whose C-terminal region is homologous to NUDT9, functions as a calcium-permeable cation channel that is highly specifically gated by ADP-ribose. These results provide molecular evidence that ADP-ribose is able to function as a second messenger in vertebrate systems through its ability to gate the TrpC7 ion channel. They are most consistent with TrpC7 functioning as a plasma membrane calcium entry channel and, therefore, with ADP-ribose functioning as a calcium entry second messenger.

Such a function is supported by the observation that ADP-ribose is able to gate a non-selective plasma membrane ion channel in the asicidian oocyte system, although this channel's properties seem distinct from those of TrpC7 (Wilding, M., et al., *Am J Physiol*, 1998, 275:C1277-83). In particular, the lower apparent affinity of TrpC7 for ADP-ribose contrasts with the ADP-ribose-gated currents described in ascidian oocytes, which were found to be gated by concentrations as low as 10 nM. This may reflect genuine ion channel differences between TrpC7 and the unidentified channels in ascidian oocytes or different ADP-ribose handling of vertebrate and invertebrate species. Alternatively, because our characterization of TrpC7 was performed in a heterologous system, TrpC7 could potentially be missing accessory proteins that contribute to gating properties. In our heterologous expression system, we also cannot entirely rule out that TrpC7 might be mistargeted (for example due to overexpression or missing accessory proteins that may be required to target TrpC7 to a subcellular compartment), and that TrpC7 might normally function solely or in part as an organellar calcium release channel.

Our results have the important implication that biological processes which produce ADP-ribose are likely to modulate calcium entry or some other novel aspect of calcium homeostasis or signaling in TrpC7-expressing cells. ADP-ribose is potentially produced in many cell biological contexts, e.g., during apoptosis through the turnover of mono-ADP-ribosylated proteins, through the action of ecto-NAD glycohydrolases such as CD38, by the breakdown of cyclic ADP-ribose, or through unknown processes present in mitochondria (McConkey, D. J. & Orrenius, S. *Stem Cells* 1996, 14:619-31; Okazaki, I. J. & Moss, J., *J Biol Chem* 1998, 273:23617-20; Koch-Nolte, F. & Haag, F., *Adv Exp Med Biol*, 1997, 419:1-13; Dousa, T. P., et al., *Am J Physiol*, 1991, 271:C1007-24; Liang, M., et al., *Arch Biochem Biophys*, 1999, 371:317-25; Chakraborti, T., et al., *Cell Signal*, 1999, 11:77-85). Therefore, the discovery of a calcium regulatory second messenger function for ADP-ribose is likely to have widespread significance.

Our data also provide a structure/function correlation that may have important implications for related ion channels. From the TrpC7 primary structure, it appears that TrpC7 evolved as a gene fusion between a TrpC7-like channel and NUDT9 or a NUDT9-like molecule. From our enzymatic data, it appears that the TrpC7 NUDT9 homology domain was altered such that it is still able to interact with ADP-ribose, but only slowly hydrolyze it. This is consistent with ADP-ribose-dependent gating of TrpC7, which was predicted by the enzymatic specificity of NUDT9, and indeed, TrpC7 gating occurs with a dose-response relationship that closely matches the $K_m$ of the isolated NUDT9 homology domain. Of course, this does not preclude alternative, yet unknown signaling mechanisms to either gate TrpC7 directly or modulate sensitivity to ADP-ribose. Based on these observations, we speculate that this implies a functional modularity of TrpC7-like channels such that the C-terminal regions of related ion channels will have similar roles in their respective gating mechanisms.

DETAILED DESCRIPTION OF THE DRAWINGS

FIG. 1: (A) Analysis of membrane currents in the presence or absence of FLAG-TrpC7 expression. The graph illustrates the temporal development of averaged membrane currents at −80 mV under various experimental conditions. Only tet-induced HEK293 cells expressing FLAG-TrpC7 generated large inward currents when perfused with 100 µM ADP-ribose (n=5±sem, closed symbols). The open symbols represent superimposed analyses of responses obtained from (i) wild-type HEK293 cells (WT) perfused with standard internal solution in the absence of ADPR (n=3±sem); (ii) uninduced cells perfused with standard internal solution in the absence of ADPR (n=5±sem); (iii) uninduced HEK293 cells perfused with standard solution supplemented with 1 mM ADPR (n=3±sem); (iv) tet-induced HEK293 cells perfused with standard internal solution without ADPR present (n=4±sem). (B) ADP-ribose induces cationic currents when FLAG-TrpC7 is expressed. HEK293 cell lines were induced to express FLAG-TrpC7 by 24 hours of treatment with 1 μg/ml of tetracycline. Intracellular perfusion by patch clamp with 300 μM ADP-ribose reliably induced almost linear cationic currents with slight outward rectification. The left panel shows, in a representative cell, the concurrent activation of inward and outward currents measured at −80 mV and +80 mV, respectively. The filled symbols indicate the time points at which individual high-resolution data traces were extracted for presentation as I/V curve in the right panel.

FIG. 2: (A) Dose-response curve for ADP-ribose-dependent gating of TrpC7. HEK293 cells expressing FLAG-TrpC7 were perfused with defined ADPR concentrations ranging from 10 μM to 1 mM, and currents were measured at −80 mV as in FIG. 1B. The maximum current amplitude of individual cells were derived by analyzing the time course of current development (see e.g., FIGS. 1A, 1B, and 1C) and fitting a Boltzmann curve to the rising phase of the developing cationic conductance. Peak current amplitudes were averaged and plotted versus ADPR concentration (n=5 to 12±sem). The averaged data points were fitted with a dose-response curve yielding an apparent $K_D$ of 90 μM and a Hill coefficient of 9.91% of all cells perfused with 60 μM ADPR or higher generated currents above control levels (n=38). (B) Kinetics of ADP-ribose-dependent gating of TrpC7. The temporal development of ADPR-gated currents was assessed as described in (a) by fitting a Boltzmann curve to the rising phase of the developing cationic conductance. The mid-point values of this analysis correspond to the time of half-maximal current activation, and are plotted as a function of ADPR concentration. (C) TrpC7 is permeable to calcium. Tet-induced HEK293 cells expressing FLAG-TrpC7 were perfused with 100 μM ADPR. 80 seconds into the experiment, and indicated by the bar, isotonic $CaCl_2$ solution (120 mM $CaCl_2$, 300 mosm) was applied externally for 20 seconds using a wide-tipped puffer pipette. The panel shows an average of inward currents from 3 cells ±sem. Note that isotonic $Ca^{2+}$ solutions are able to support about 50% of current previously carried mainly by $Na^+$ ions.

TABLE I

Sequences with partial homologies to mutTCCH-1

Sequences with GenBank accession numbers:

S80361, U90552, AJ009303, U23484, AF064847, AF043518, AB006621, AF027205, D50406, AF022992, Z36802, AF005158, AF030560, AF053713, AI565810.1, AI202187, AI420725.1, AI421550.1, AI492458.1, AA151649, AA449304, AA478767, AI051366, AA421840, AI149797, AA526157, AA640299, N70512, AA644080, AA151730, W16856, W05526, AI376380, AA317639, AI339649, AA449561, AI473395.1, AI473262.1, AI538140, R69093, AI361086, AA472987, AA038761, AA118873, AA164146, AA109494, AA796970, AA555692, AI120864, AA611152, AI462474, AA199307, AA022129, AA277950, AI529730, Z31052, AI304013, AA023309, AA260732, AI316627, AA286351, Z31093, W45957, AI225788, AA409783, AA638286, AA408526, AI550568.1, AA560671, Q09297, P52006, P35942, Q23236, P10902, BAA34700, BAA17285, BAA19270.

All references disclosed herein are incorporated by reference in their entirety. What is claimed is presented below and is followed by a Sequence Listing.

I claim:

1. A method for identifying an agent useful in modulating ion transport across a calcium channel, comprising:
   (a) adding to a calcium channel polypeptide comprising the amino acid sequence of wild type TrpC7 polypeptide or SEQ ID NO:6 and having a calcium channel and a mutT domain, an amount of exogenous ADP-ribose that is capable of increasing ion transport across the calcium channel;
   (b) contacting the calcium channel polypeptide with a candidate agent suspected of modulating calcium channel activity of the polypeptide;
   (c) measuring the ion transport across the calcium channel, and
   (d) comparing the measured ion transport across the calcium channel to a control to determine whether the candidate agent modulates ion transport across the calcium channel, wherein a difference in the measured ion transport across the calcium channel in the presence of the candidate agent compared to the control indicates the agent modulates ion transport across the calcium channel.

2. The method of claim 1, wherein the polypeptide comprising a calcium channel and a mutT domain is a polypeptide encoded by the nucleic acid of SEQ ID NO:5.

3. The method of claim 1 wherein the ion transported across the calcium channel is a Ca, Mg, Zn, Sr, or Mn ion.

4. The method of claim 1, wherein the polypeptide comprising a calcium channel and a mutT domain has a sequence of amino acids as set forth in SEQ ID NO:6.

5. The method of claim 1, where the control is a calcium channel polypeptide as in (a) that is not contacted with the candidate agent.

6. The method of claim 1, wherein an increase in calcium channel activity relative to the control indicates that the candidate agent is an agent that increases calcium channel activity.

7. The method of claim 1, wherein a decrease in calcium channel activity relative to the control indicates that the candidate agent is an agent that decreases calcium channel activity.

* * * * *

SEQUENCE LISTING

```
<160> NUMBER OF SEQ ID NOS: 11

<210> SEQ ID NO 1
<211> LENGTH: 1718
<212> TYPE: DNA
<213> ORGANISM: Homo sapiens
<220> FEATURE:
<221> NAME/KEY: CDS
<222> LOCATION: (326)..(1375)
<220> FEATURE:
<221> NAME/KEY: Unsure
<222> LOCATION: (1442)
<223> OTHER INFORMATION: a or c or g or t/u

<400> SEQUENCE: 1
gcggacgcgt gggcggacgc gtggggaaag ttacgaggtt cgtggccgcg gtttccccag      60
gcagctggcg ctggaggctt cggcgtcacg tgctggtctg gatttttctc gatgcactgg     120
ggaaagcggt ggactcttat cgtgggaggg ctcttgatct gtgatttata gataggcaca     180
gctactcccg ttcgggaacc caacggcaga caggtcctag tgcccatcag atacccgcgg     240
ccgggactcg gagctgtggg gtgtggggag gcggaggcac caactaagag cgacctagca     300
tcgcaaagcc gccctcgggg cgctc atg gcg gga cgc ctc ctg gga aag gct      352
                              Met Ala Gly Arg Leu Leu Gly Lys Ala
                              1               5 tta gcc gcg gtg tct ctc tct ctg gcc ttg gcc tct gtg act atc agg      400
Leu Ala Ala Val Ser Leu Ser Leu Ala Leu Ala Ser Val Thr Ile Arg
10              15                  20                  25 tcc tcg cgc tgc cgc ggc atc cag gcg ttc aga aac tcg ttt tca tct      448
Ser Ser Arg Cys Arg Gly Ile Gln Ala Phe Arg Asn Ser Phe Ser Ser
                30                  35                  40
```

-continued

| | |
|---|---|
| tct tgg ttt cat ctt aat acc aac gtc atg tct ggt tct aat ggt tcc<br>Ser Trp Phe His Leu Asn Thr Asn Val Met Ser Gly Ser Asn Gly Ser<br>              45                    50                    55 | 496 |
| aaa gaa aat tct cac aat aag gct cgg acg tct cct tac cca ggt tca<br>Lys Glu Asn Ser His Asn Lys Ala Arg Thr Ser Pro Tyr Pro Gly Ser<br>              60                    65                    70 | 544 |
| aaa gtt gaa cga agc cag gtt cct aat gag aaa gtg ggc tgg ctt gtt<br>Lys Val Glu Arg Ser Gln Val Pro Asn Glu Lys Val Gly Trp Leu Val<br>75                    80                    85 | 592 |
| gag tgg caa gac tat aag cct gtg gaa tac act gca gtc tct gtc ttg<br>Glu Trp Gln Asp Tyr Lys Pro Val Glu Tyr Thr Ala Val Ser Val Leu<br>90                    95                 100          105 | 640 |
| gct gga ccc agg tgg gca gat cct cag atc agt gaa agt aat ttt tct<br>Ala Gly Pro Arg Trp Ala Asp Pro Gln Ile Ser Glu Ser Asn Phe Ser<br>             110                   115                120 | 688 |
| ccc aag ttt aac gaa aag gat ggg cat gtt gag aga aag agc aag aat<br>Pro Lys Phe Asn Glu Lys Asp Gly His Val Glu Arg Lys Ser Lys Asn<br>             125                   130                135 | 736 |
| ggc ctg tat gag att gaa aat gga aga ccg aga aat cct gca gga cgg<br>Gly Leu Tyr Glu Ile Glu Asn Gly Arg Pro Arg Asn Pro Ala Gly Arg<br>             140                   145                150 | 784 |
| act gga ctg gtg ggc cgg ggg ctt ttg ggg cga tgg ggc cca aat cac<br>Thr Gly Leu Val Gly Arg Gly Leu Leu Gly Arg Trp Gly Pro Asn His<br>155                   160                   165 | 832 |
| gct gca gat ccc att ata acc aga tgg aaa agg gat agc agt gga aat<br>Ala Ala Asp Pro Ile Ile Thr Arg Trp Lys Arg Asp Ser Ser Gly Asn<br>170                   175                   180                185 | 880 |
| aaa atc atg cat cct gtt tct ggg aag cat atc tta caa ttt gtt gca<br>Lys Ile Met His Pro Val Ser Gly Lys His Ile Leu Gln Phe Val Ala<br>             190                   195                200 | 928 |
| ata aaa agg aaa gac tgt gga gaa tgg gca atc cca ggg ggg atg gtg<br>Ile Lys Arg Lys Asp Cys Gly Glu Trp Ala Ile Pro Gly Gly Met Val<br>                205                   210                215 | 976 |
| gat cca gga gag aag att agt gcc aca ctg aaa aga gaa ttt ggt gag<br>Asp Pro Gly Glu Lys Ile Ser Ala Thr Leu Lys Arg Glu Phe Gly Glu<br>                220                   225                230 | 1024 |
| gaa gct ctc aac tcc tta cag aaa acc agt gct gag aag aga gaa ata<br>Glu Ala Leu Asn Ser Leu Gln Lys Thr Ser Ala Glu Lys Arg Glu Ile<br>235                   240                   245 | 1072 |
| gag gaa aag ttg cac aaa ctc ttc agc caa gac cac cta gtg ata tat<br>Glu Glu Lys Leu His Lys Leu Phe Ser Gln Asp His Leu Val Ile Tyr<br>250                   255                   260                265 | 1120 |
| aag gga tat gtt gat gat cct cga aac act gat aat gca tgg atg gag<br>Lys Gly Tyr Val Asp Asp Pro Arg Asn Thr Asp Asn Ala Trp Met Glu<br>                 270                   275                280 | 1168 |
| aca gaa gct gtg aac tac cat gac gaa aca ggt gag ata atg gat aat<br>Thr Glu Ala Val Asn Tyr His Asp Glu Thr Gly Glu Ile Met Asp Asn<br>                285                   290                295 | 1216 |
| ctt atg cta gaa gct gga gat gat gct gga aaa gtg aaa tgg gtg gac<br>Leu Met Leu Glu Ala Gly Asp Asp Ala Gly Lys Val Lys Trp Val Asp<br>             300                   305                310 | 1264 |
| atc aat gat aaa ctg aag ctt tat gcc agt cac tct caa ttc atc aaa<br>Ile Asn Asp Lys Leu Lys Leu Tyr Ala Ser His Ser Gln Phe Ile Lys<br>315                   320                   325 | 1312 |
| ctt gtg gct gag aaa cga gat gca cac tgg agc gag gac tct gaa gct<br>Leu Val Ala Glu Lys Arg Asp Ala His Trp Ser Glu Asp Ser Glu Ala<br>330                   335                   340                345 | 1360 |
| gac tgc cat gcg ttg tagctgatgg tctccgtgta agccaaaggc ccacagagga<br>Asp Cys His Ala Leu<br>             350 | 1415 |

-continued

```
gcatatactg aaaagaaggc agtatcncag aatttatact ataaaaaggg cagggtaggc    1475
cacttggcct atttactttc aaaacaattt gcatttagag tgtttcgcat cagaataaca    1535
tgagtaagat gaactggaac acaaaatttt cagctctttg gtcaaaagga atataagtaa    1595
tcatattttg tatgtattcg atttaagcat ggcttaaatt aaatttaaac aactaatgct    1655
ctttgaagaa tcataatcag aataaagata aattcttgat cagctataaa aaaaaaaaaa    1715
aaa                                                                  1718
```

<210> SEQ ID NO 2
<211> LENGTH: 350
<212> TYPE: PRT
<213> ORGANISM: Homo sapiens
<220> FEATURE:
<221> NAME/KEY: DOMAIN
<222> LOCATION: (210)...(234)
<223> OTHER INFORMATION: Nudix Box

<400> SEQUENCE: 2

```
Met Ala Gly Arg Leu Leu Gly Lys Ala Leu Ala Ala Val Ser Leu Ser
1               5                   10                  15

Leu Ala Leu Ala Ser Val Thr Ile Arg Ser Ser Arg Cys Arg Gly Ile
            20                  25                  30

Gln Ala Phe Arg Asn Ser Phe Ser Ser Trp Phe His Leu Asn Thr
        35                  40                  45

Asn Val Met Ser Gly Ser Asn Gly Ser Lys Glu Asn Ser His Asn Lys
    50                  55                  60

Ala Arg Thr Ser Pro Tyr Pro Gly Ser Lys Val Glu Arg Ser Gln Val
65                  70                  75                  80

Pro Asn Glu Lys Val Gly Trp Leu Val Glu Trp Gln Asp Tyr Lys Pro
                85                  90                  95

Val Glu Tyr Thr Ala Val Ser Val Leu Ala Gly Pro Arg Trp Ala Asp
            100                 105                 110

Pro Gln Ile Ser Glu Ser Asn Phe Ser Pro Lys Phe Asn Glu Lys Asp
        115                 120                 125

Gly His Val Glu Arg Lys Ser Lys Asn Gly Leu Tyr Glu Ile Glu Asn
    130                 135                 140

Gly Arg Pro Arg Asn Pro Ala Gly Arg Thr Gly Leu Val Gly Arg Gly
145                 150                 155                 160

Leu Leu Gly Arg Trp Gly Pro Asn His Ala Ala Asp Pro Ile Thr
                165                 170                 175

Arg Trp Lys Arg Asp Ser Ser Gly Asn Lys Ile Met His Pro Val Ser
            180                 185                 190

Gly Lys His Ile Leu Gln Phe Val Ala Ile Lys Arg Lys Asp Cys Gly
        195                 200                 205

Glu Trp Ala Ile Pro Gly Gly Met Val Asp Pro Gly Glu Lys Ile Ser
    210                 215                 220

Ala Thr Leu Lys Arg Glu Phe Gly Glu Glu Ala Leu Asn Ser Leu Gln
225                 230                 235                 240

Lys Thr Ser Ala Glu Lys Arg Glu Ile Glu Lys Leu His Lys Leu
                245                 250                 255

Phe Ser Gln Asp His Leu Val Ile Tyr Lys Gly Tyr Val Asp Asp Pro
            260                 265                 270

Arg Asn Thr Asp Asn Ala Trp Met Glu Thr Glu Ala Val Asn Tyr His
        275                 280                 285

Asp Glu Thr Gly Glu Ile Met Asp Asn Leu Met Leu Glu Ala Gly Asp
    290                 295                 300
```

```
Asp Ala Gly Lys Val Lys Trp Val Asp Ile Asn Asp Lys Leu Lys Leu
305                 310                 315                 320

Tyr Ala Ser His Ser Gln Phe Ile Lys Leu Val Ala Glu Lys Arg Asp
                325                 330                 335

Ala His Trp Ser Glu Asp Ser Glu Ala Asp Cys His Ala Leu
            340                 345                 350

<210> SEQ ID NO 3
<211> LENGTH: 1050
<212> TYPE: DNA
<213> ORGANISM: Homo sapiens

<400> SEQUENCE: 3
atggcgggac gcctcctggg aaaggcttta gccgcggtgt ctctctctct ggccttggcc    60
tctgtgacta tcaggtcctc gcgctgccgc ggcatccagg cgttcagaaa ctcgttttca   120
tcttcttggt ttcatcttaa taccaacgtc atgtctggtt ctaatggttc caaagaaaat   180
tctcacaata aggctcggac gtctccttac ccaggttcaa aagttgaacg aagccaggtt   240
cctaatgaga agtgggctg gcttgttgag tggcaagact ataagcctgt ggaatacact   300
gcagtctctg tcttggctgg acccaggtgg gcagatcctc agatcagtga agtaattttt   360
tctcccaagt ttaacgaaaa ggatgggcat gttgagagaa agagcaagaa tggcctgtat   420
gagattgaaa atggaagacc gagaaatcct gcaggacgga ctggactggt gggccggggg   480 cttttgggg gatggggccc aaatcacgct gcagatccca ttataaccag atggaaaagg   540
gatagcagtg gaaataaaat catgcatcct gtttctggga agcatatctt acaatttgtt   600
gcaataaaaa ggaaagactg tggagaatgg gcaatcccag gggggatggt ggatccagga   660
gagaagatta gtgccacact gaaaagagaa tttggtgagg aagctctcaa ctccttacag   720
aaaaccagtg ctgagaagag agaaatagag gaaaagttgc acaaactctt cagccaagac   780
cacctagtga tatataaggg atatgttgat gatcctcgaa acactgataa tgcatggatg   840
gagacagaag ctgtgaacta ccatgacgaa acaggtgaga taatggataa tcttatgcta   900
gaagctggag atgatgctgg aaaagtgaaa tgggtggaca tcaatgataa actgaagctt   960
tatgccagtc actctcaatt catcaaactt gtggctgaga acgagatgc acactggagc  1020 gaggactctg aagctgactg ccatgcgttg                                    1050

<210> SEQ ID NO 4
<211> LENGTH: 23
<212> TYPE: PRT
<213> ORGANISM: Homo sapiens
<220> FEATURE:
<221> NAME/KEY: VARIANT
<222> LOCATION: (2)..(6)
<223> OTHER INFORMATION: Any Amino Acid
<220> FEATURE:
<221> NAME/KEY: VARIANT
<222> LOCATION: (8)..(14)
<223> OTHER INFORMATION: Any Amino Acid
<220> FEATURE:
<221> NAME/KEY: VARIANT
<222> LOCATION: (17)
<223> OTHER INFORMATION: Amino Acid with Aliphatic Side Chain
<220> FEATURE:
<221> NAME/KEY: VARIANT
<222> LOCATION: (18)
<223> OTHER INFORMATION: Any Amino Acid
<220> FEATURE:
<221> NAME/KEY: VARIANT
<222> LOCATION: (21)..(22)
<223> OTHER INFORMATION: Any Amino Acid
<220> FEATURE:
```

```
<221> NAME/KEY: VARIANT
<222> LOCATION: (23)
<223> OTHER INFORMATION: Amino Acid with Aliphatic Side Chain

<400> SEQUENCE: 4

Gly Xaa Xaa Xaa Xaa Glu Xaa Xaa Xaa Xaa Xaa Xaa Xaa Arg Glu
1               5                   10                  15

Xaa Xaa Glu Glu Xaa Xaa Xaa
            20

<210> SEQ ID NO 5
<211> LENGTH: 6220
<212> TYPE: DNA
<213> ORGANISM: Homo sapiens
<220> FEATURE:
<221> NAME/KEY: CDS
<222> LOCATION: (446)..(4954)

<400> SEQUENCE: 5
```

| | | |
|---|---|---|
| tgtgcagaat tgtacagttg cgaaaccatg tcgctggcag ctggtgctgg cggtggagac | 60 |
| ttccctgtgc ggtgctcagt gcatctgcac ccgtggggga gggagctctt tctctggccc | 120 |
| tgcagtcacc tgaggttgtt accattatga acggccgctg gaccccccgc atgtgcatgt | 180 |
| actcccccag agtgtccggg ggccccagcc aagggacaca tctcacgcag ctgggaacat | 240 |
| gtgcaggctg atgaagagaa ccggatgagg gcttcacatg aggaagcatg tggccaggtc | 300 |
| ctctcagaac atcagcctca tcttcctgtc tctgatctat ttcaccaacc accccatgtg | 360 |
| tctctagaac cccagtgtag cgagctggag agaggactgt cctgagggca gcaggcctgg | 420 |
| ttgcagctgg cgtgggggtc tcaga atg gag ccc tca gcc ctg agg aaa gct | 472 |
|                                 Met Glu Pro Ser Ala Leu Arg Lys Ala |
|                                  1               5 |
| ggc tcg gag cag gag gag ggc ttt gag ggg ctg ccc aga agg gtc act | 520 |
| Gly Ser Glu Gln Glu Glu Gly Phe Glu Gly Leu Pro Arg Arg Val Thr |
|  10              15                  20                  25 |
| gac ctg ggg atg gtc tcc aat ctc cgg cgc agc aac agc agc ctc ttc | 568 |
| Asp Leu Gly Met Val Ser Asn Leu Arg Arg Ser Asn Ser Ser Leu Phe |
|                 30                  35                  40 |
| aag agc tgg agg cta cag tgc ccc ttc ggc aac aat gac aag caa gaa | 616 |
| Lys Ser Trp Arg Leu Gln Cys Pro Phe Gly Asn Asn Asp Lys Gln Glu |
|             45                  50                  55 |
| agc ctc agt tcg tgg att cct gaa aac atc aag aag aaa gaa tgc gtg | 664 |
| Ser Leu Ser Ser Trp Ile Pro Glu Asn Ile Lys Lys Lys Glu Cys Val |
|         60                  65                  70 |
| tat ttt gtg gaa agt tcc aaa ctg tct gat gct ggg aag gtg gtg tgt | 712 |
| Tyr Phe Val Glu Ser Ser Lys Leu Ser Asp Ala Gly Lys Val Val Cys |
|     75                  80                  85 |
| cag tgt ggc tac acg cat gag cag cac ttg gag gag gct acc aag ccc | 760 |
| Gln Cys Gly Tyr Thr His Glu Gln His Leu Glu Glu Ala Thr Lys Pro |
|  90                  95                  100                 105 |
| cac acc ttc cag ggc aca cag tgg gac cca aag aaa cat gtc cag gag | 808 |
| His Thr Phe Gln Gly Thr Gln Trp Asp Pro Lys Lys His Val Gln Glu |
|                 110                 115                 120 |
| atg cca acc gat gcc ttt ggc gac atc gtc ttc acg ggc ctg agc cag | 856 |
| Met Pro Thr Asp Ala Phe Gly Asp Ile Val Phe Thr Gly Leu Ser Gln |
|             125                 130                 135 |
| aag gtg aaa aag tac gtc cga gtc tcc cag gac acg ccc tcc agc gtg | 904 |
| Lys Val Lys Lys Tyr Val Arg Val Ser Gln Asp Thr Pro Ser Ser Val |
|         140                 145                 150 |
| atc tac cac ctc atg acc cag cac tgg ggg ctg gac gtc ccc aat ctc | 952 |
| Ile Tyr His Leu Met Thr Gln His Trp Gly Leu Asp Val Pro Asn Leu |
|     155                 160                 165 |

```
ttg atc tcg gtg acc ggg ggg gcc aag aac ttc aac atg aag ccg cgg     1000
Leu Ile Ser Val Thr Gly Gly Ala Lys Asn Phe Asn Met Lys Pro Arg
170             175                 180                 185 ctg aag agc att ttc cgc aga ggc ctg gtc aag gtg gct cag acc aca     1048
Leu Lys Ser Ile Phe Arg Arg Gly Leu Val Lys Val Ala Gln Thr Thr
                190                 195                 200 ggg gcc tgg atc atc aca ggg ggg tcc cac acc ggc gtc atg aag cag     1096
Gly Ala Trp Ile Ile Thr Gly Gly Ser His Thr Gly Val Met Lys Gln
            205                 210                 215 gta ggc gag gcg gtg cgg gac ttc agc ctg agc agc agc tac aag gaa     1144
Val Gly Glu Ala Val Arg Asp Phe Ser Leu Ser Ser Ser Tyr Lys Glu
        220                 225                 230 ggc gag ctc atc acc atc gga gtc gcc acc tgg ggc act gtc cac cgc     1192
Gly Glu Leu Ile Thr Ile Gly Val Ala Thr Trp Gly Thr Val His Arg
    235                 240                 245 cgc gag ggc ctg atc cat ccc acg ggc agc ttc ccc gcc gag tac ata     1240
Arg Glu Gly Leu Ile His Pro Thr Gly Ser Phe Pro Ala Glu Tyr Ile
250                 255                 260                 265 ctg gat gag gat ggc caa ggg aac ctg acc tgc cta gac agc aac cac     1288
Leu Asp Glu Asp Gly Gln Gly Asn Leu Thr Cys Leu Asp Ser Asn His
                270                 275                 280 tct cac ttc atc ctc gtg gac gac ggg acc cac ggc cag tac ggg gtg     1336
Ser His Phe Ile Leu Val Asp Asp Gly Thr His Gly Gln Tyr Gly Val
            285                 290                 295 gag att cct ctg agg acc agg ctg gag aag ttc ata tcg gag cag acc     1384
Glu Ile Pro Leu Arg Thr Arg Leu Glu Lys Phe Ile Ser Glu Gln Thr
        300                 305                 310 aag gaa aga gga ggt gtg gcc atc aag atc ccc atc gtg tgc gtg gtg     1432
Lys Glu Arg Gly Gly Val Ala Ile Lys Ile Pro Ile Val Cys Val Val
    315                 320                 325 ctg gag ggc ggc ccg ggc acg ttg cac acc atc gac aac gcc acc acc     1480
Leu Glu Gly Gly Pro Gly Thr Leu His Thr Ile Asp Asn Ala Thr Thr
330                 335                 340                 345 aac ggc acc ccc tgt gtg gtt gtg gag ggc tcg ggc cgc gtg gcc gac     1528
Asn Gly Thr Pro Cys Val Val Val Glu Gly Ser Gly Arg Val Ala Asp
                350                 355                 360 gtc att gcc cag gtg gcc aac ctg cct gtc tcg gac atc act atc tcc     1576
Val Ile Ala Gln Val Ala Asn Leu Pro Val Ser Asp Ile Thr Ile Ser
            365                 370                 375 ctg atc cag cag aaa ctg agc gtg ttc ttc cag gag atg ttt gag acc     1624
Leu Ile Gln Gln Lys Leu Ser Val Phe Phe Gln Glu Met Phe Glu Thr
        380                 385                 390 ttc acg gaa agc agg att gtc gag tgg acc aaa aag atc caa gat att     1672
Phe Thr Glu Ser Arg Ile Val Glu Trp Thr Lys Lys Ile Gln Asp Ile
    395                 400                 405 gtc cgg agg cgg cag ctg ctg act gtc ttc cgg gaa ggc aag gat ggt     1720
Val Arg Arg Arg Gln Leu Leu Thr Val Phe Arg Glu Gly Lys Asp Gly
410                 415                 420                 425 cag cag gac gtg gat gtg gcc atc ttg cag gcc ttg ctg aaa gcc tca     1768
Gln Gln Asp Val Asp Val Ala Ile Leu Gln Ala Leu Leu Lys Ala Ser
                430                 435                 440 cgg agc caa gac cac ttt ggc cac gag aac tgg gac cac cag ctg aaa     1816
Arg Ser Gln Asp His Phe Gly His Glu Asn Trp Asp His Gln Leu Lys
            445                 450                 455 ctg gca gtg gca tgg aat cgc gtg gac att gcc cgc agt gag atc ttc     1864
Leu Ala Val Ala Trp Asn Arg Val Asp Ile Ala Arg Ser Glu Ile Phe
        460                 465                 470 atg gat gag tgg cag tgg aag cct tca gat ctg cac ccc acg atg aca     1912
Met Asp Glu Trp Gln Trp Lys Pro Ser Asp Leu His Pro Thr Met Thr
    475                 480                 485
```

```
gct gca ctc atc tcc aac aag cct gag ttt gtg aag ctc ttc ctg gaa    1960
Ala Ala Leu Ile Ser Asn Lys Pro Glu Phe Val Lys Leu Phe Leu Glu
490             495                 500                 505 aac ggg gtg cag ctg aag gag ttt gtc acc tgg gac acc ttg ctc tac    2008
Asn Gly Val Gln Leu Lys Glu Phe Val Thr Trp Asp Thr Leu Leu Tyr
                510                 515                 520 ctg tac gag aac ctg gac ccc tcc tgc ctg ttc cac agc aag ctg caa    2056
Leu Tyr Glu Asn Leu Asp Pro Ser Cys Leu Phe His Ser Lys Leu Gln
            525                 530                 535 aag gtg ctg gtg gag gat ccc gag cgc ccg gct tgc gcg ccc gcg gcg    2104
Lys Val Leu Val Glu Asp Pro Glu Arg Pro Ala Cys Ala Pro Ala Ala
        540                 545                 550 ccc cgc ctg cag atg cac cac gtg gcc cag gtg ctg cgg gag ctg ctg    2152
Pro Arg Leu Gln Met His His Val Ala Gln Val Leu Arg Glu Leu Leu
555                 560                 565 ggg gac ttc acg cag ccg ctt tat ccc cgg ccc cgg cac aac gac cgg    2200
Gly Asp Phe Thr Gln Pro Leu Tyr Pro Arg Pro Arg His Asn Asp Arg
570                 575                 580                 585 ctg cgg ctc ctg ctg ccc gtt ccc cac gtc aag ctc aac gtg cag gga    2248
Leu Arg Leu Leu Leu Pro Val Pro His Val Lys Leu Asn Val Gln Gly
                590                 595                 600 gtg agc ctc cgg tcc ctc tac aag cgt tcc tca ggc cat gtg acc ttc    2296
Val Ser Leu Arg Ser Leu Tyr Lys Arg Ser Ser Gly His Val Thr Phe
            605                 610                 615 acc atg gac ccc atc cgt gac ctt ctc att tgg gcc att gtc cag aac    2344
Thr Met Asp Pro Ile Arg Asp Leu Leu Ile Trp Ala Ile Val Gln Asn
        620                 625                 630 cgt cgg gag ctg gca gga atc atc tgg gct cag agc cag gac tgc atc    2392
Arg Arg Glu Leu Ala Gly Ile Ile Trp Ala Gln Ser Gln Asp Cys Ile
635                 640                 645 gca gcg gcc ttg gcc tgc agc aag atc ctg aag gaa ctg tcc aag gag    2440
Ala Ala Ala Leu Ala Cys Ser Lys Ile Leu Lys Glu Leu Ser Lys Glu
650                 655                 660                 665 gag gag gac acg gac agc tcg gag gag atg ctg gcg ctg gcg gag gag    2488
Glu Glu Asp Thr Asp Ser Ser Glu Glu Met Leu Ala Leu Ala Glu Glu
                670                 675                 680 tat gag cac aga gcc atc ggg gtc ttc acc gag tgc tac cgg aag gac    2536
Tyr Glu His Arg Ala Ile Gly Val Phe Thr Glu Cys Tyr Arg Lys Asp
            685                 690                 695 gaa gag aga gcc cag aaa ctg ctc acc cgc gtg tcc gag gcc tgg ggg    2584
Glu Glu Arg Ala Gln Lys Leu Leu Thr Arg Val Ser Glu Ala Trp Gly
        700                 705                 710 aag acc acc tgc ctg cag ctg gcc ctg gag gcc aag gac atg aag ttt    2632
Lys Thr Thr Cys Leu Gln Leu Ala Leu Glu Ala Lys Asp Met Lys Phe
715                 720                 725 gtg tct cac ggg ggc atc cag gcc ttc ctg acc aag gtg tgg tgg ggc    2680
Val Ser His Gly Gly Ile Gln Ala Phe Leu Thr Lys Val Trp Trp Gly
730                 735                 740                 745 cag ctc tcc gtg gac aat ggg ctg tgg cgt gtg acc ctg tgc atg ctg    2728
Gln Leu Ser Val Asp Asn Gly Leu Trp Arg Val Thr Leu Cys Met Leu
                750                 755                 760 gcc ttc ccg ctg ctc ctc acc ggc ctc atc tcc ttc agg gag aag agg    2776
Ala Phe Pro Leu Leu Leu Thr Gly Leu Ile Ser Phe Arg Glu Lys Arg
            765                 770                 775 ctg cag gat gtg ggc acc ccc gcg gcc cgc gcc cgt gcc ttc ttc acc    2824
Leu Gln Asp Val Gly Thr Pro Ala Ala Arg Ala Arg Ala Phe Phe Thr
        780                 785                 790 gca ccc gtg gtg gtc ttc cac ctg aac atc ctc tcc tac ttc gcc ttc    2872
Ala Pro Val Val Val Phe His Leu Asn Ile Leu Ser Tyr Phe Ala Phe
795                 800                 805
```

-continued

```
ctc tgc ctg ttc gcc tac gtg ctc atg gtg gac ttc cag cct gtg ccc    2920
Leu Cys Leu Phe Ala Tyr Val Leu Met Val Asp Phe Gln Pro Val Pro
810             815                 820                 825 tcc tgg tgc gag tgt gcc atc tac ctc tgg ctc ttc tcc ttg gtg tgc    2968
Ser Trp Cys Glu Cys Ala Ile Tyr Leu Trp Leu Phe Ser Leu Val Cys
        830                 835                 840 gag gag atg cgg cag ctc ttc tat gac cct gac gag tgc ggg ctg atg    3016
Glu Glu Met Arg Gln Leu Phe Tyr Asp Pro Asp Glu Cys Gly Leu Met
            845                 850                 855 aag aag gca gcc ttg tac ttc agt gac ttc tgg aat aag ctg gac gtc    3064
Lys Lys Ala Ala Leu Tyr Phe Ser Asp Phe Trp Asn Lys Leu Asp Val
860             865                 870 ggc gca atc ttg ctc ttc gtg gca ggg ctg acc tgc agg ctc atc ccg    3112
Gly Ala Ile Leu Leu Phe Val Ala Gly Leu Thr Cys Arg Leu Ile Pro
    875                 880                 885 gcg acg ctg tac ccc ggg cgc gtc atc ctc tct ctg gac ttc atc ctg    3160
Ala Thr Leu Tyr Pro Gly Arg Val Ile Leu Ser Leu Asp Phe Ile Leu
890             895                 900                 905 ttc tgc ctc cgg ctc atg cac att ttt acc atc agt aag acg ctg ggg    3208
Phe Cys Leu Arg Leu Met His Ile Phe Thr Ile Ser Lys Thr Leu Gly
                910                 915                 920 ccc aag atc atc att gtg aag cgg atg atg aag gac gtc ttc ttc ttc    3256
Pro Lys Ile Ile Ile Val Lys Arg Met Met Lys Asp Val Phe Phe Phe
        925                 930                 935 ctc ttc ctg ctg gct gtg tgg gtg gtg tcc ttc ggg gtg gcc aag cag    3304
Leu Phe Leu Leu Ala Val Trp Val Val Ser Phe Gly Val Ala Lys Gln
            940                 945                 950 gcc atc ctc atc cac aac gag cgc cgg gtg gac tgg ctg ttc cga ggg    3352
Ala Ile Leu Ile His Asn Glu Arg Arg Val Asp Trp Leu Phe Arg Gly
955                 960                 965 gcc gtc tac cac tcc tac ctc acc atc ttc ggg cag atc ccg ggc tac    3400
Ala Val Tyr His Ser Tyr Leu Thr Ile Phe Gly Gln Ile Pro Gly Tyr
970             975                 980                 985 atc gac ggt gtg aac ttc aac ccg gag cac tgc agc ccc aat ggc acc    3448
Ile Asp Gly Val Asn Phe Asn Pro Glu His Cys Ser Pro Asn Gly Thr
                990                 995                 1000 gac ccc tac aag cct aag tgc ccc gag agc gac gcg acg cag cag        3493
Asp Pro Tyr Lys Pro Lys Cys Pro Glu Ser Asp Ala Thr Gln Gln
        1005                1010                1015 agg ccg gcc ttc cct gag tgg ctg acg gtc ctc cta ctc tgc ctc        3538
Arg Pro Ala Phe Pro Glu Trp Leu Thr Val Leu Leu Leu Cys Leu
    1020                1025                1030 tac ctg ctc ttc acc aac atc ctg ctg ctc aac ctc ctc atc gcc        3583
Tyr Leu Leu Phe Thr Asn Ile Leu Leu Leu Asn Leu Leu Ile Ala
1035                1040                1045 atg ttc aac tac acc ttc cag cag gtg cag gag cac acg gac cag        3628
Met Phe Asn Tyr Thr Phe Gln Gln Val Gln Glu His Thr Asp Gln
        1050                1055                1060 att tgg aag ttc cag cgc cat gac ctg atc gag gag tac cac ggc        3673
Ile Trp Lys Phe Gln Arg His Asp Leu Ile Glu Glu Tyr His Gly
    1065                1070                1075 cgc ccc gcc gcg ccg ccc ccc ttc atc ctc ctc agc cac ctg cag        3718
Arg Pro Ala Ala Pro Pro Pro Phe Ile Leu Leu Ser His Leu Gln
1080                1085                1090 ctc ttc atc aag agg gtg gtc ctg aag act ccg gcc aag agg cac        3763
Leu Phe Ile Lys Arg Val Val Leu Lys Thr Pro Ala Lys Arg His
        1095                1100                1105 aag cag ctc aag aac aag ctg gag aag aac gag gag gcg gcc ctg        3808
Lys Gln Leu Lys Asn Lys Leu Glu Lys Asn Glu Glu Ala Ala Leu
    1110                1115                1120
```

-continued

| | | |
|---|---|---|
| cta tcc tgg gag atc tac ctg aag gag aac tac ctc cag aac cga<br>Leu Ser Trp Glu Ile Tyr Leu Lys Glu Asn Tyr Leu Gln Asn Arg<br>1125                    1130                    1135 | | 3853 |
| cag ttc cag caa aag cag cgg ccc gag cag aag atc gag gac atc<br>Gln Phe Gln Gln Lys Gln Arg Pro Glu Gln Lys Ile Glu Asp Ile<br>1140                    1145                    1150 | | 3898 |
| agc aat aag gtt gac gcc atg gtg gac ctg ctg gac ctg gac cca<br>Ser Asn Lys Val Asp Ala Met Val Asp Leu Leu Asp Leu Asp Pro<br>1155                    1160                    1165 | | 3943 |
| ctg aag agg tcg ggc tcc atg gag cag agg ttg gcc tcc ctg gag<br>Leu Lys Arg Ser Gly Ser Met Glu Gln Arg Leu Ala Ser Leu Glu<br>1170                    1175                    1180 | | 3988 |
| gag cag gtg gcc cag aca gcc cga gcc ctg cac tgg atc gtg agg<br>Glu Gln Val Ala Gln Thr Ala Arg Ala Leu His Trp Ile Val Arg<br>1185                    1190                    1195 | | 4033 |
| acg ctg cgg gcc agc ggc ttc agc tcg gag gcg gac gtc ccc act<br>Thr Leu Arg Ala Ser Gly Phe Ser Ser Glu Ala Asp Val Pro Thr<br>1200                    1205                    1210 | | 4078 |
| ctg gcc tcc cag aag gcc gcg gag gag ccg gat gct gag ccg gga<br>Leu Ala Ser Gln Lys Ala Ala Glu Glu Pro Asp Ala Glu Pro Gly<br>1215                    1220                    1225 | | 4123 |
| ggc agg aag aag acg gag gag ccg ggc gac agc tac cac gtg aat<br>Gly Arg Lys Lys Thr Glu Glu Pro Gly Asp Ser Tyr His Val Asn<br>1230                    1235                    1240 | | 4168 |
| gcc cgg cac ctc ctc tac ccc aac tgc cct gtc acg cgc ttc ccc<br>Ala Arg His Leu Leu Tyr Pro Asn Cys Pro Val Thr Arg Phe Pro<br>1245                    1250                    1255 | | 4213 |
| gtg ccc aac gag aag gtg ccc tgg gag acg gag ttc ctg atc tat<br>Val Pro Asn Glu Lys Val Pro Trp Glu Thr Glu Phe Leu Ile Tyr<br>1260                    1265                    1270 | | 4258 |
| gac cca ccc ttt tac acg gca gag agg aag gac gcg gcc gcc atg<br>Asp Pro Pro Phe Tyr Thr Ala Glu Arg Lys Asp Ala Ala Ala Met<br>1275                    1280                    1285 | | 4303 |
| gac ccc atg gga gac acc ctg gag cca ctg tcc acg atc cag tac<br>Asp Pro Met Gly Asp Thr Leu Glu Pro Leu Ser Thr Ile Gln Tyr<br>1290                    1295                    1300 | | 4348 |
| aac gtg gtg gat ggc ctg agg gac cgc cgg agc ttc cac ggg ccg<br>Asn Val Val Asp Gly Leu Arg Asp Arg Arg Ser Phe His Gly Pro<br>1305                    1310                    1315 | | 4393 |
| tac aca gtg cag gcc ggg ttg ccc ctg aac ccc atg ggc cgc aca<br>Tyr Thr Val Gln Ala Gly Leu Pro Leu Asn Pro Met Gly Arg Thr<br>1320                    1325                    1330 | | 4438 |
| gga ctg cgt ggg cgc ggg agc ctc agc tgc ttc gga ccc aac cac<br>Gly Leu Arg Gly Arg Gly Ser Leu Ser Cys Phe Gly Pro Asn His<br>1335                    1340                    1345 | | 4483 |
| acg ctg tac ccc atg gtc acg cgg tgg agg cgg aac gag gat gga<br>Thr Leu Tyr Pro Met Val Thr Arg Trp Arg Arg Asn Glu Asp Gly<br>1350                    1355                    1360 | | 4528 |
| gcc atc tgc agg aag agc ata aag aag atg ctg gaa gtg ctg gtg<br>Ala Ile Cys Arg Lys Ser Ile Lys Lys Met Leu Glu Val Leu Val<br>1365                    1370                    1375 | | 4573 |
| gtg aag ctc cct ctc tcc gag cac tgg gcc ctg cct ggg ggc tcc<br>Val Lys Leu Pro Leu Ser Glu His Trp Ala Leu Pro Gly Gly Ser<br>1380                    1385                    1390 | | 4618 |
| cgg gag cca ggg gag atg cta cct cgg aag ctg aag cgg atc ctc<br>Arg Glu Pro Gly Glu Met Leu Pro Arg Lys Leu Lys Arg Ile Leu<br>1395                    1400                    1405 | | 4663 |
| cgg cag gag cac tgg ccg tct ttt gaa aac ttg ctg aag tgc ggc<br>Arg Gln Glu His Trp Pro Ser Phe Glu Asn Leu Leu Lys Cys Gly<br>1410                    1415                    1420 | | 4708 |

| | | | | | | | | | | | | | | |
|---|---|---|---|---|---|---|---|---|---|---|---|---|---|---|
| atg | gag | gtg | tac | aaa | ggc | tac | atg | gat | gac | ccg | agg | aac | acg | gac | 4753 |
| Met | Glu | Val | Tyr | Lys | Gly | Tyr | Met | Asp | Asp | Pro | Arg | Asn | Thr | Asp | |
| | | | 1425 | | | | 1430 | | | | | 1435 | | | |
| aat | gcc | tgg | atc | gag | acg | gtg | gcc | gtc | agc | gtc | cac | ttc | cag | gac | 4798 |
| Asn | Ala | Trp | Ile | Glu | Thr | Val | Ala | Val | Ser | Val | His | Phe | Gln | Asp | |
| | | | 1440 | | | | 1445 | | | | | 1450 | | | |
| cag | aat | gac | gtg | gag | ctg | aac | agg | ctg | aac | tct | aac | ctg | cac | gcc | 4843 |
| Gln | Asn | Asp | Val | Glu | Leu | Asn | Arg | Leu | Asn | Ser | Asn | Leu | His | Ala | |
| | | | 1455 | | | | 1460 | | | | | 1465 | | | |
| tgc | gac | tcg | ggg | gcc | tcc | atc | cga | tgg | cag | gtg | gtg | gac | agg | cgc | 4888 |
| Cys | Asp | Ser | Gly | Ala | Ser | Ile | Arg | Trp | Gln | Val | Val | Asp | Arg | Arg | |
| | | | 1470 | | | | 1475 | | | | | 1480 | | | |
| atc | cca | ctc | tat | gcg | aac | cac | aag | acc | ctc | ctc | cag | aag | gca | gcc | 4933 |
| Ile | Pro | Leu | Tyr | Ala | Asn | His | Lys | Thr | Leu | Leu | Gln | Lys | Ala | Ala | |
| | | | 1485 | | | | 1490 | | | | | 1495 | | | |
| gct | gag | ttc | ggg | gct | cac | tac | tgactgtgcc | ctcaggctgg | gcggctccag | | | | | | 4984 |
| Ala | Glu | Phe | Gly | Ala | His | Tyr | | | | | | | | | |
| | | | 1500 | | | | | | | | | | | | |

| | |
|---|---|
| tccatagacg ttccccccag aaaccagggc ttctctctcc tgagcctggc caggactcag | 5044 |
| gctgttcctg ggccctgcac atgatggggt ttggtggacc cagtgcccct cacgcctgcc | 5104 |
| gcaagtctgc tgcagatgac ctcatgaact ggaaggggtc aaggtgaccc gggaggagag | 5164 |
| ctcaagacag gcacaggct actcagagct gaggggcccc tgggacccttggccatcagg | 5224 |
| cgaggggctg ggcctgtgca gctgggccct tggccagagt ccactcccttcctggctgtg | 5284 |
| tcaccccgag cagctcatcc accatggagg tcattggcct gaggcaagtt ccccggagag | 5344 |
| tcgggatccc ctgtggcccc tcaggcctatgtctgtgag aagggggccc tgccactctc | 5404 |
| cccaagaggg cctccatgtt tcgaggtgcc tcaacatgga gccttgcctg gcctgggcta | 5464 |
| ggggcactgt ctgaactcct gactgtcagg ataaactccg tgggggtaca ggagcccaga | 5524 |
| caaagcccag gcctgtcaag agacgcagag ggccctgcc agggttggcc cagggaccc | 5584 |
| tgggacgagg ctgcagaagc tctccctccc tactccctgg gagccacgtg ctggccatgt | 5644 |
| ggccagggac ggcatgagca ggaggcgggg acgtgggggc cttctggttt ggtgtcaaca | 5704 |
| gctcacagga gcgtgaacca tgagggccct caggagggga acgtggtaaa acccaagaca | 5764 |
| ttaaatctgc catctcaggc ctggctggct cttctgtgct ttccacaaat aaagttcctg | 5824 |
| acacgtccag ggccagggc tgtgtgacgg ctgcctgaag ttctcctcga tccccggtg | 5884 |
| agcttcctgc agcctgtgga tgtcctgcag ccctcagcc ctaccccaa gtttctcctc | 5944 |
| tgacccatca gctccctgtc ttcatttcc taaacctggg ctccagcatc gtccccaagc | 6004 |
| ccaccaggcc aggatgcagg catccacatg ccctcctcct tggcttcccc tgcgtggtgg | 6064 |
| tgccaatgtg ccctggcacc cctgcagagg ctccggatgg agcctgggc tgcctggcca | 6124 |
| ctgagcactg gccgaggtga tgcccaccct tccctggaca ggcctctgtc ttccacctga | 6184 |
| cccaaagctc tctagccacc cccttgtccc cagtat | 6220 |

<210> SEQ ID NO 6
<211> LENGTH: 1503
<212> TYPE: PRT
<213> ORGANISM: Homo sapiens
<220> FEATURE:
<221> NAME/KEY: DOMAIN
<222> LOCATION: (1385)...(1409)
<223> OTHER INFORMATION: Nudix Box

<400> SEQUENCE: 6

Met Glu Pro Ser Ala Leu Arg Lys Ala Gly Ser Glu Gln Glu Glu Gly

-continued

```
1               5               10              15
Phe Glu Gly Leu Pro Arg Arg Val Thr Asp Leu Gly Met Val Ser Asn
                20              25              30

Leu Arg Arg Ser Asn Ser Ser Leu Phe Lys Ser Trp Arg Leu Gln Cys
            35              40              45

Pro Phe Gly Asn Asn Asp Lys Gln Glu Ser Leu Ser Ser Trp Ile Pro
    50              55              60

Glu Asn Ile Lys Lys Glu Cys Val Tyr Phe Val Glu Ser Ser Lys
65              70              75              80

Leu Ser Asp Ala Gly Lys Val Val Cys Gln Cys Gly Tyr Thr His Glu
            85              90              95

Gln His Leu Glu Glu Ala Thr Lys Pro His Thr Phe Gln Gly Thr Gln
            100             105             110

Trp Asp Pro Lys Lys His Val Gln Glu Met Pro Thr Asp Ala Phe Gly
            115             120             125

Asp Ile Val Phe Thr Gly Leu Ser Gln Lys Val Lys Lys Tyr Val Arg
            130             135             140

Val Ser Gln Asp Thr Pro Ser Ser Val Ile Tyr His Leu Met Thr Gln
145             150             155             160

His Trp Gly Leu Asp Val Pro Asn Leu Leu Ile Ser Val Thr Gly Gly
            165             170             175

Ala Lys Asn Phe Asn Met Lys Pro Arg Leu Lys Ser Ile Phe Arg Arg
            180             185             190

Gly Leu Val Lys Val Ala Gln Thr Thr Gly Ala Trp Ile Ile Thr Gly
            195             200             205

Gly Ser His Thr Gly Val Met Lys Gln Val Gly Glu Ala Val Arg Asp
            210             215             220

Phe Ser Leu Ser Ser Ser Tyr Lys Glu Gly Glu Leu Ile Thr Ile Gly
225             230             235             240

Val Ala Thr Trp Gly Thr Val His Arg Arg Glu Gly Leu Ile His Pro
            245             250             255

Thr Gly Ser Phe Pro Ala Glu Tyr Ile Leu Asp Glu Asp Gly Gln Gly
            260             265             270

Asn Leu Thr Cys Leu Asp Ser Asn His Ser His Phe Ile Leu Val Asp
            275             280             285

Asp Gly Thr His Gly Gln Tyr Gly Val Glu Ile Pro Leu Arg Thr Arg
            290             295             300

Leu Glu Lys Phe Ile Ser Glu Gln Thr Lys Glu Arg Gly Gly Val Ala
305             310             315             320

Ile Lys Ile Pro Ile Val Cys Val Val Leu Glu Gly Gly Pro Gly Thr
            325             330             335

Leu His Thr Ile Asp Asn Ala Thr Thr Asn Gly Thr Pro Cys Val Val
            340             345             350

Val Glu Gly Ser Gly Arg Val Ala Asp Val Ile Ala Gln Val Ala Asn
            355             360             365

Leu Pro Val Ser Asp Ile Thr Ile Ser Leu Ile Gln Gln Lys Leu Ser
            370             375             380

Val Phe Phe Gln Glu Met Phe Glu Thr Phe Thr Glu Ser Arg Ile Val
385             390             395             400

Glu Trp Thr Lys Lys Ile Gln Asp Ile Val Arg Arg Arg Gln Leu Leu
            405             410             415

Thr Val Phe Arg Glu Gly Lys Asp Gly Gln Gln Asp Val Asp Val Ala
            420             425             430
```

```
Ile Leu Gln Ala Leu Leu Lys Ala Ser Arg Ser Gln Asp His Phe Gly
        435                 440                 445

His Glu Asn Trp Asp His Gln Leu Lys Leu Ala Val Ala Trp Asn Arg
    450                 455                 460

Val Asp Ile Ala Arg Ser Glu Ile Phe Met Asp Glu Trp Gln Trp Lys
465                 470                 475                 480

Pro Ser Asp Leu His Pro Thr Met Thr Ala Ala Leu Ile Ser Asn Lys
                485                 490                 495

Pro Glu Phe Val Lys Leu Phe Leu Glu Asn Gly Val Gln Leu Lys Glu
                500                 505                 510

Phe Val Thr Trp Asp Thr Leu Leu Tyr Leu Tyr Glu Asn Leu Asp Pro
            515                 520                 525

Ser Cys Leu Phe His Ser Lys Leu Gln Lys Val Leu Val Glu Asp Pro
    530                 535                 540

Glu Arg Pro Ala Cys Ala Pro Ala Ala Pro Arg Leu Gln Met His His
545                 550                 555                 560

Val Ala Gln Val Leu Arg Glu Leu Leu Gly Asp Phe Thr Gln Pro Leu
                565                 570                 575

Tyr Pro Arg Pro Arg His Asn Asp Arg Leu Arg Leu Leu Leu Pro Val
                580                 585                 590

Pro His Val Lys Leu Asn Val Gln Gly Val Ser Leu Arg Ser Leu Tyr
            595                 600                 605

Lys Arg Ser Ser Gly His Val Thr Phe Thr Met Asp Pro Ile Arg Asp
    610                 615                 620

Leu Leu Ile Trp Ala Ile Val Gln Asn Arg Arg Glu Leu Ala Gly Ile
625                 630                 635                 640

Ile Trp Ala Gln Ser Gln Asp Cys Ile Ala Ala Leu Ala Cys Ser
                645                 650                 655

Lys Ile Leu Lys Glu Leu Ser Lys Glu Glu Asp Thr Asp Ser Ser
                660                 665                 670

Glu Glu Met Leu Ala Leu Ala Glu Glu Tyr Glu His Arg Ala Ile Gly
            675                 680                 685

Val Phe Thr Glu Cys Tyr Arg Lys Asp Glu Glu Arg Ala Gln Lys Leu
    690                 695                 700

Leu Thr Arg Val Ser Glu Ala Trp Gly Lys Thr Thr Cys Leu Gln Leu
705                 710                 715                 720

Ala Leu Glu Ala Lys Asp Met Lys Phe Val Ser His Gly Gly Ile Gln
                725                 730                 735

Ala Phe Leu Thr Lys Val Trp Trp Gly Gln Leu Ser Val Asp Asn Gly
            740                 745                 750

Leu Trp Arg Val Thr Leu Cys Met Leu Ala Phe Pro Leu Leu Leu Thr
    755                 760                 765

Gly Leu Ile Ser Phe Arg Glu Lys Arg Leu Gln Asp Val Gly Thr Pro
770                 775                 780

Ala Ala Arg Ala Arg Ala Phe Phe Thr Ala Pro Val Val Val Phe His
785                 790                 795                 800

Leu Asn Ile Leu Ser Tyr Phe Ala Phe Leu Cys Leu Phe Ala Tyr Val
                805                 810                 815

Leu Met Val Asp Phe Gln Pro Val Pro Ser Trp Cys Glu Cys Ala Ile
                820                 825                 830

Tyr Leu Trp Leu Phe Ser Leu Val Cys Glu Glu Met Arg Gln Leu Phe
            835                 840                 845

Tyr Asp Pro Asp Glu Cys Gly Leu Met Lys Lys Ala Ala Leu Tyr Phe
            850                 855                 860
```

-continued

```
Ser Asp Phe Trp Asn Lys Leu Asp Val Gly Ala Ile Leu Leu Phe Val
865                 870                 875                 880

Ala Gly Leu Thr Cys Arg Leu Ile Pro Ala Thr Leu Tyr Pro Gly Arg
                885                 890                 895

Val Ile Leu Ser Leu Asp Phe Ile Leu Phe Cys Leu Arg Leu Met His
            900                 905                 910

Ile Phe Thr Ile Ser Lys Thr Leu Gly Pro Lys Ile Ile Ile Val Lys
        915                 920                 925

Arg Met Met Lys Asp Val Phe Phe Leu Phe Leu Leu Ala Val Trp
    930                 935                 940

Val Val Ser Phe Gly Val Ala Lys Gln Ala Ile Leu Ile His Asn Glu
945                 950                 955                 960

Arg Arg Val Asp Trp Leu Phe Arg Gly Ala Val Tyr His Ser Tyr Leu
                965                 970                 975

Thr Ile Phe Gly Gln Ile Pro Gly Tyr Ile Asp Gly Val Asn Phe Asn
            980                 985                 990

Pro Glu His Cys Ser Pro Asn Gly Thr Asp Pro Tyr Lys Pro Lys Cys
        995                 1000                1005

Pro Glu Ser Asp Ala Thr Gln Gln Arg Pro Ala Phe Pro Glu Trp
1010                1015                1020

Leu Thr Val Leu Leu Leu Cys Leu Tyr Leu Leu Phe Thr Asn Ile
1025                1030                1035

Leu Leu Leu Asn Leu Leu Ile Ala Met Phe Asn Tyr Thr Phe Gln
1040                1045                1050

Gln Val Gln Glu His Thr Asp Gln Ile Trp Lys Phe Gln Arg His
1055                1060                1065

Asp Leu Ile Glu Glu Tyr His Gly Arg Pro Ala Ala Pro Pro Pro
1070                1075                1080

Phe Ile Leu Leu Ser His Leu Gln Leu Phe Ile Lys Arg Val Val
1085                1090                1095

Leu Lys Thr Pro Ala Lys Arg His Lys Gln Leu Lys Asn Lys Leu
1100                1105                1110

Glu Lys Asn Glu Glu Ala Ala Leu Leu Ser Trp Glu Ile Tyr Leu
1115                1120                1125

Lys Glu Asn Tyr Leu Gln Asn Arg Gln Phe Gln Gln Lys Gln Arg
1130                1135                1140

Pro Glu Gln Lys Ile Glu Asp Ile Ser Asn Lys Val Asp Ala Met
1145                1150                1155

Val Asp Leu Leu Asp Leu Asp Pro Leu Lys Arg Ser Gly Ser Met
1160                1165                1170

Glu Gln Arg Leu Ala Ser Leu Glu Glu Gln Val Ala Gln Thr Ala
1175                1180                1185

Arg Ala Leu His Trp Ile Val Arg Thr Leu Arg Ala Ser Gly Phe
1190                1195                1200

Ser Ser Glu Ala Asp Val Pro Thr Leu Ala Ser Gln Lys Ala Ala
1205                1210                1215

Glu Glu Pro Asp Ala Glu Pro Gly Gly Arg Lys Lys Thr Glu Glu
1220                1225                1230

Pro Gly Asp Ser Tyr His Val Asn Ala Arg His Leu Leu Tyr Pro
1235                1240                1245

Asn Cys Pro Val Thr Arg Phe Pro Val Pro Asn Glu Lys Val Pro
1250                1255                1260

Trp Glu Thr Glu Phe Leu Ile Tyr Asp Pro Pro Phe Tyr Thr Ala
```

|  |  |  |  |  |  |  |  |  |  |
|---|---|---|---|---|---|---|---|---|---|
|  | 1265 |  |  | 1270 |  |  |  | 1275 |  |

Glu Arg Lys Asp Ala Ala Met Asp Pro Met Gly Asp Thr Leu
1280                1285                    1290

Glu Pro Leu Ser Thr Ile Gln Tyr Asn Val Val Asp Gly Leu Arg
    1295                1300                1305

Asp Arg Arg Ser Phe His Gly Pro Tyr Thr Val Gln Ala Gly Leu
1310                1315                    1320

Pro Leu Asn Pro Met Gly Arg Thr Gly Leu Arg Gly Arg Gly Ser
    1325                1330                1335

Leu Ser Cys Phe Gly Pro Asn His Thr Leu Tyr Pro Met Val Thr
1340                1345                    1350

Arg Trp Arg Arg Asn Glu Asp Gly Ala Ile Cys Arg Lys Ser Ile
    1355                1360                1365

Lys Lys Met Leu Glu Val Leu Val Val Lys Leu Pro Leu Ser Glu
1370                1375                    1380

His Trp Ala Leu Pro Gly Gly Ser Arg Glu Pro Gly Glu Met Leu
    1385                1390                1395

Pro Arg Lys Leu Lys Arg Ile Leu Arg Gln Glu His Trp Pro Ser
1400                1405                    1410

Phe Glu Asn Leu Leu Lys Cys Gly Met Glu Val Tyr Lys Gly Tyr
    1415                1420                1425

Met Asp Asp Pro Arg Asn Thr Asp Asn Ala Trp Ile Glu Thr Val
1430                1435                    1440

Ala Val Ser Val His Phe Gln Asp Gln Asn Asp Val Glu Leu Asn
    1445                1450                1455

Arg Leu Asn Ser Asn Leu His Ala Cys Asp Ser Gly Ala Ser Ile
1460                1465                    1470

Arg Trp Gln Val Val Asp Arg Arg Ile Pro Leu Tyr Ala Asn His
    1475                1480                1485

Lys Thr Leu Leu Gln Lys Ala Ala Ala Glu Phe Gly Ala His Tyr
1490                1495                    1500

<210> SEQ ID NO 7
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: PCR primer; Homo sapiens

<400> SEQUENCE: 7
cagtgtggct acacgcatga                                          20

<210> SEQ ID NO 8
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: PCR primer; Homo sapiens

<400> SEQUENCE: 8
tcaggcccgt gaagacgatg                                          20

<210> SEQ ID NO 9
<211> LENGTH: 20
<212> TYPE: DNA
<213> ORGANISM: Artificial Sequence

```
<220> FEATURE:
<221> NAME/KEY: primer_bind
<222> LOCATION: (1)..(20)
<223> OTHER INFORMATION: PCR primer; Homo sapiens

<400> SEQUENCE: 9
ggcaagacta taagcctgtg                                               20

<210> SEQ ID NO 10
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: PCR primer; Homo sapiens

<400> SEQUENCE: 10
ataatgggat ctgcagcgtg                                               20

<210> SEQ ID NO 11
<211> LENGTH: 14
<212> TYPE: PRT
<213> ORGANISM: Artificial Sequence
<220> FEATURE:
<221> NAME/KEY: DOMAIN
<222> LOCATION: (1)..(14)
<223> OTHER INFORMATION: FLAG epitope

<400> SEQUENCE: 11

Met Gly Asp Tyr Lys Asp Asp Asp Lys Arg Pro Leu Ala
1               5                   10
```